(12) United States Patent
Naba et al.

(10) Patent No.: US 10,433,723 B2
(45) Date of Patent: Oct. 8, 2019

(54) CONTROL APPARATUS, IMAGING CONTROL METHOD, AND STORAGE MEDIUM

(71) Applicant: CANON KABUSHIKI KAISHA, Tokyo (JP)

(72) Inventors: Takashi Naba, Kawasaki (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/799,048

(22) Filed: Oct. 31, 2017

(65) Prior Publication Data

US 2018/0064331 A1 Mar. 8, 2018

Related U.S. Application Data

(63) Continuation of application No. 13/431,797, filed on Mar. 27, 2012, now Pat. No. 9,839,350.

(30) Foreign Application Priority Data

Mar. 31, 2011 (JP) ................. 2011-079362
Jan. 25, 2012 (JP) ................. 2012-013037

(51) Int. Cl.
*A61B 3/10* (2006.01)
*A61B 3/12* (2006.01)
(Continued)

(52) U.S. Cl.
CPC ................ *A61B 3/102* (2013.01); *A61B 3/10* (2013.01); *A61B 3/12* (2013.01); *A61B 3/0025* (2013.01);
(Continued)

(58) Field of Classification Search
CPC ......... A61B 3/102; A61B 3/12; A61B 3/0025; A61B 3/1005; A61B 3/14; A61B 5/0066;
(Continued)

(56) References Cited

U.S. PATENT DOCUMENTS 5,889,576 A * 3/1999 Fujieda .................. A61B 3/152
351/208
7,643,154 B2 * 1/2010 Kikawa .................... A61B 3/10
356/497

(Continued)

FOREIGN PATENT DOCUMENTS

JP H11-299738 A 11/1999
JP 2008-161406 A 7/2008
(Continued)

*Primary Examiner* — Allen C Wong
(74) *Attorney, Agent, or Firm* — Canon U.S.A., Inc., IP Division

(57) ABSTRACT

A control apparatus of an imaging apparatus, includes a selection unit configured to select an image-capturing site of a subject to be examined, a control unit configured to control adjustment of a member of the imaging apparatus, according to the selected image-capturing site, and a determination unit configured to determine whether to perform the adjustment or not in response to a change of image-capturing sites through the selection by the selection unit, based on image-capturing conditions for the image-capturing sites before and after the change of the image-capturing sites.

32 Claims, 19 Drawing Sheets

(51) Int. Cl.
  *A61B 3/14* (2006.01)
  *G01B 9/02* (2006.01)
  *A61B 3/00* (2006.01)
  *A61B 5/00* (2006.01)
  *A61B 3/18* (2006.01)

(52) U.S. Cl.
  CPC ............... *A61B 3/1005* (2013.01); *A61B 3/14* (2013.01); *A61B 3/18* (2013.01); *A61B 5/0066* (2013.01); *A61B 5/0073* (2013.01); *G01B 9/02091* (2013.01)

(58) Field of Classification Search
  CPC ........... A61B 5/0073; A61B 3/10; A61B 3/18; G01B 9/02091
  USPC .......................................................... 348/78
  See application file for complete search history.

(56) References Cited

U.S. PATENT DOCUMENTS

| | | | | |
|---|---|---|---|---|
| 7,880,895 B2* | 2/2011 | Yamada | ................. | A61B 3/102 356/479 |
| 2008/0151256 A1* | 6/2008 | Kikawa | ................... | A61B 3/10 356/496 |
| 2009/0268161 A1* | 10/2009 | Hart | ...................... | A61B 3/102 351/208 |
| 2010/0157311 A1* | 6/2010 | Hayashi | ............. | G01N 21/4795 356/496 |
| 2010/0302550 A1* | 12/2010 | Hacker | ................. | A61B 3/1005 356/479 |
| 2010/0315590 A1* | 12/2010 | Ueno | ................... | A61B 3/0058 351/206 |
| 2011/0102802 A1* | 5/2011 | Izatt | ...................... | A61B 3/102 356/479 |
| 2011/0205490 A1* | 8/2011 | Murata | .................. | A61B 3/102 351/206 |
| 2011/0262037 A1* | 10/2011 | Ohnishi | ................. | H04N 19/61 382/166 |
| 2011/0273669 A1* | 11/2011 | Abitbol | ................ | A61B 3/1015 351/212 |
| 2011/0299034 A1* | 12/2011 | Walsh | .................... | A61B 3/102 351/206 |
| 2012/0083667 A1* | 4/2012 | Isogai | .................... | A61B 3/102 600/300 |
| 2012/0121158 A1* | 5/2012 | Sekine | ............... | G01N 21/4795 382/131 |

FOREIGN PATENT DOCUMENTS

| | | |
|---|---|---|
| JP | 2009-172155 A | 8/2009 |
| JP | 2009-291252 A | 12/2009 |
| JP | 2010-012109 A | 1/2010 |
| JP | 2010-169502 A | 8/2010 |

* cited by examiner

FIG. 8

| IMAGE-CAPTURING MODE | FIXATION LIGHT POSITION | COHERENCE GATE POSITION |
|---|---|---|
| MACULAR GLAUCOMA | MACULA | VITREOUS BODY |
| AMD | MACULA | CHOROID MEMBRANE |
| OPTIC DISC GLAUCOMA | OPTIC DISC | VITREOUS BODY |

FIG. 9

| ITEM | PERIOD OF TIME (sec) |
|---|---|
| OCT FOCUS ADJUSTMENT | 7 |
| COHERENCE GATE ADJUSTMENT | 9 |
| ANTERIOR EYE ALIGNMENT | 15 |
| SHIFTING BETWEEN RIGHT AND LEFT EYES | 20 |

FIG. 10

| SELECTION | IMAGE-CAPTURING MODE | FIXATION LIGHT POSITION | COHERENCE GATE POSITION | RIGHT EYE OR LEFT EYE | COMMENT |
|---|---|---|---|---|---|
| MODE 1 | MACULAR GLAUCOMA | MACULA | VITREOUS BODY | LEFT | FOR GLAUCOMA DIAGNOSIS |
| MODE 2 | AMD | MACULA | CHOROID MEMBRANE | LEFT | FOR AMD DIAGNOSIS |
| MODE 3 | OPTIC DISC GLAUCOMA | OPTIC DISC | VITREOUS BODY | LEFT | FOR GLAUCOMA DIAGNOSIS |
| MODE 4 | MACULAR GLAUCOMA | MACULA | VITREOUS BODY | RIGHT | FOR COMPARISON BETWEEN RIGHT AND LEFT EYES |

FIG. 11

| MODE ORDER | SHIFTING BETWEEN RIGHT EYE AND LEFT EYES | CHANGE OF FIXATION LIGHT | ALIGNMENT | FOCUS | CG |
|---|---|---|---|---|---|
| 1-2-3-4 | ○××○ | ○×○○ | ○×○○ | ○×○○ | ○○○○ |
| 1-2-4-3 | ○×○○ | ○×××○ | ○×○○ | ○×○○ | ○○○○ |
| 1-3-2-4 | ○××○ | ○○○× | ○○○○ | ○○○○ | ○○○○ |
| 1-3-4-2 | ○×○○ | ○○○× | ○○○○ | ○○○○ | ○○○○ |
| 1-4-2-3 | ○○×× | ○×××○ | ○○×○ | ○○×○ | ○○○○ |
| 1-4-3-2 | ○○×× | ○×○○ | ○○○○ | ○○○○ | ○○○○ |
| 2-1-3-4 | ○××○ | ○×○○ | ○×○○ | ○×○○ | ○○○○ |
| 2-1-4-3 | ○×○○ | ○××○ | ○×○○ | ○×○○ | ○○○○ |
| 2-3-1-4 | ○××○ | ○○○× | ○○○○ | ○○○○ | ○○○○ |
| 2-3-4-1 | ○×○○ | ○○○× | ○○○○ | ○○○○ | ○○○○ |
| 2-4-1-3 | ○○×× | ○××○ | ○○×○ | ○○×○ | ○○×○ |
| 2-4-3-1 | ○○×× | ○×○○ | ○○○○ | ○○○○ | ○○○○ |
| 3-1-2-4 | ○××○ | ○○×× | ○○×○ | ○○×○ | ○○○○ |
| 3-1-4-2 | ○×○○ | ○○×× | ○○○○ | ○○○○ | ○○○○ |
| 3-2-1-4 | ○××○ | ○○×× | ○○×○ | ○○×○ | ○○○○ |
| 3-2-4-1 | ○×○○ | ○○×× | ○○○○ | ○○○○ | ○○○○ |
| 3-4-1-2 | ○○×× | ○○×× | ○○×× | ○○×× | ○○×○ |
| 3-4-2-1 | ○○×× | ○○×× | ○○×× | ○○×× | ○○○○ |
| 4-1-2-3 | ○○×× | ○××○ | ○○×○ | ○○×○ | ○○○○ |
| 4-1-3-2 | ○○×× | ○×○○ | ○○○○ | ○○○○ | ○○○○ |
| 4-2-1-3 | ○○×× | ○××○ | ○○×○ | ○○×○ | ○○○○ |
| 4-2-3-1 | ○○×× | ○×○○ | ○○○○ | ○○○○ | ○○○○ |
| 4-3-1-2 | ○○×× | ○○○× | ○○○× | ○○○× | ○○○○ |
| 4-3-2-1 | ○○×× | ○○○× | ○○○× | ○○○× | ○○○○ |

FIG. 12

| MODE ORDER | NUMBER OF TIMES OF SHIFTING BETWEEN RIGHT EYE AND LEFT EYES | ALIGNMENT | FOCUS | CG | ADJUSTMENT PERIOD OF TIME (sec) |
|---|---|---|---|---|---|
| 1-2-3-4 | 2 | 3 | 3 | 4 | 142 |
| 1-2-4-3 | 3 | 3 | 3 | 4 | 162 |
| 1-3-2-4 | 2 | 4 | 4 | 4 | 164 |
| 1-3-4-2 | 3 | 4 | 4 | 4 | 184 |
| 1-4-2-3 | 2 | 3 | 3 | 4 | 142 |
| 1-4-3-2 | 2 | 4 | 4 | 4 | 164 |
| 2-1-3-4 | 2 | 3 | 3 | 4 | 142 |
| 2-1-4-3 | 3 | 3 | 3 | 4 | 162 |
| 2-3-1-4 | 2 | 4 | 4 | 4 | 164 |
| 2-3-4-1 | 3 | 4 | 4 | 4 | 184 |
| 2-4-1-3 | 2 | 3 | 3 | 3 | 133 |
| 2-4-3-1 | 2 | 4 | 4 | 4 | 164 |
| 3-1-2-4 | 2 | 3 | 3 | 4 | 142 |
| 3-1-4-2 | 3 | 4 | 4 | 4 | 184 |
| 3-2-1-4 | 2 | 3 | 3 | 4 | 142 |
| 3-2-4-1 | 3 | 4 | 4 | 4 | 184 |
| 3-4-1-2 | 2 | 2 | 2 | 3 | 111 |
| 3-4-2-1 | 2 | 2 | 2 | 4 | 120 |
| 4-1-2-3 | 2 | 3 | 3 | 4 | 142 |
| 4-1-3-2 | 2 | 4 | 4 | 4 | 164 |
| 4-2-1-3 | 2 | 3 | 3 | 4 | 142 |
| 4-2-3-1 | 2 | 4 | 4 | 4 | 164 |
| 4-3-1-2 | 2 | 3 | 3 | 4 | 142 |
| 4-3-2-1 | 2 | 3 | 3 | 4 | 142 |

CONTROL APPARATUS, IMAGING CONTROL METHOD, AND STORAGE MEDIUM

CROSS REFERENCE TO RELATED APPLICATIONS

This application is a continuation application of U.S. patent application Ser. No. 13/431,797 filed on Mar. 27, 2012 which claims priority from Japanese Patent Application No. 2011-079362 filed Mar. 31, 2011 and Japanese Patent Application No. 2012-013037 filed Jan. 25, 2012, all of which hereby incorporated by reference herein in their entirety.

BACKGROUND

Technical Field

The present disclosure relates to a control apparatus that controls adjustment performed in an imaging apparatus, an image-capturing control method thereof, and a storage medium recording a program for executing an image-capturing control process.

Currently, various ophthalmic apparatuses equipped with an optical apparatus are used. For example, as the optical apparatuses for eye observation, various apparatuses such as anterior eye imaging apparatuses, fundus cameras, Scanning Laser Ophthalmoscopes (SLOs) are used.

Among those apparatuses, an Optical Coherence Tomography (OCT) apparatus (hereinafter referred to as an OCT apparatus) provides a high resolution tomogram of a sample, and is now becoming essential an essential piece of ophthalmic equipment for retinal outpatient departments.

The OCT apparatus emits a low coherent light beam to irradiate a sample, so that the light beam reflected by the sample interferes with a reference light beam to be measured at high sensitivity. The OCT apparatus also scans the sample using the low coherent light beam to provide a high resolution tomogram of the sample. Accordingly, a tomogram of a retina at a fundus of a subject's eye can be captured at high resolution by the OCT apparatus. As a result, OCT apparatuses have been widely used for ophthalmologic examination of retinae.

An ophthalmic apparatus that captures images of a retina needs to align an optical system thereof with a subject's pupil, and to focus on the subject's fundus. In the OCT apparatus, interference of a light beam reflected by the retina with a reference light beam obtained by way of a reference object is used, and therefore, it is necessary to adjust the optical path length of the reference light beam. Conventionally, the path length has been manually adjusted, but in recent years, some apparatuses have been invented to achieve automatic adjustment of the path length for highly efficient image capturing.

U.S. Pat. No. 5,889,576 discusses a technique of an ophthalmic apparatus, in which alignment is automatically adjusted by determining an alignment reference point based on a pupil position detected from a signal from an imaging unit and an index image from a cornea, by moving a measuring unit.

U.S. Pat. No. 7,880,895 discusses a technique of an optical tomographic apparatus, in which a reference optical path is changed between, in a retinal mode, high resolution imaging of a retinal surface side portion and, in a choroidal mode, high resolution imaging of a choroid membrane side portion, to automatically obtain images.

Whether adjustment is performed manually or automatically, any change in imaging position of a subject's optic disc or macula or any change in image-capturing mode requires readjustment, which increases loads on an operator and prolongs the period of time required before imaging.

SUMMARY

According to some embodiments, a control apparatus equipped in an imaging apparatus is provided. The control apparatus comprising: a selection unit configured to select an image-capturing site of a test object; a control unit configured to control adjustment of a member of the imaging apparatus, corresponding to the selected image-capturing site; a determination unit configured to determine whether to perform the adjustment or not in response to an exchange of image-capturing sites through the selection, based on image-capturing conditions for the image-capturing sites before and after the exchange.

According to another embodiment, an imaging apparatus includes a control apparatus. The control apparatus controls an imaging apparatus that performs Optical Coherence Tomography, and includes a changing unit configured to switch image-capturing modes for capturing images of a subject's eye, a determination unit configured to determine whether to cause the imaging apparatus to perform a specific adjustment in response to the mode change, based on the image-capturing modes before and after the change, and a control unit configured to perform the control of the specific adjustment based on the determination result.

Further features and aspects of the present disclosure will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 8 is a table illustrating a relationship between an image-capturing mode, a fixation light position, and a coherence gate position.

FIG. 9 is a table illustrating a relationship between adjustment items and periods of time required for the adjustments, respectively.

FIG. 10 is a view illustrating an example of setting illustrating each image capturing mode according to an exemplary embodiment.

FIG. 11 is a view illustrating whether adjustment is required or not for each adjustment item, with marks "o" and "X", for each order of image capturing.

FIG. 12 is a view illustrating the number of times of adjustments for each adjustment item and total period of time required for the adjustments, for each order of image capturing.

DESCRIPTION OF THE EMBODIMENTS

Various exemplary embodiments, features, and aspects will be described in detail below with reference to the drawings.

Figure 1:
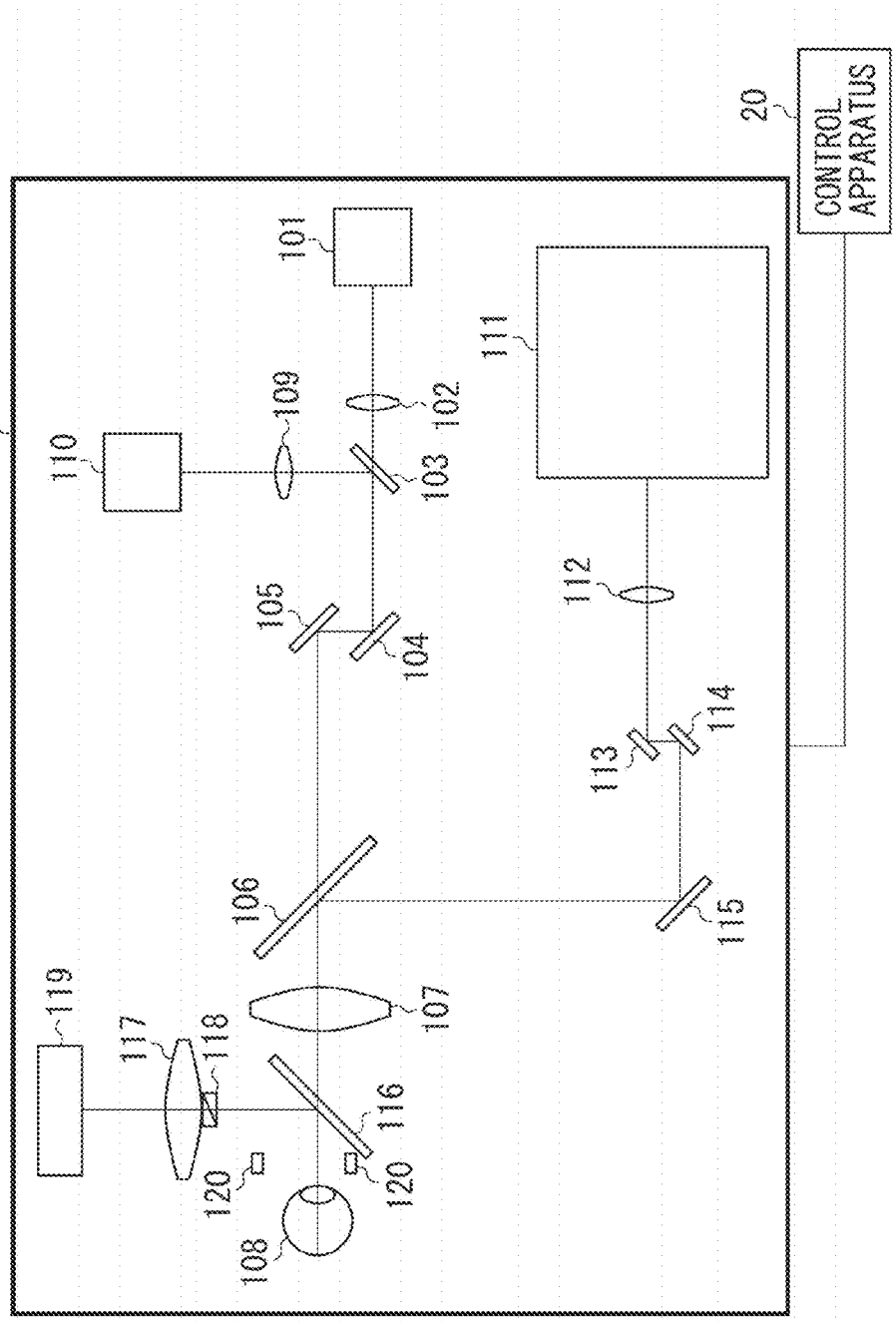
FIG. 1 is a block diagram illustrating a structure of an image diagnosis system according to an exemplary embodiment.
Figure 2:
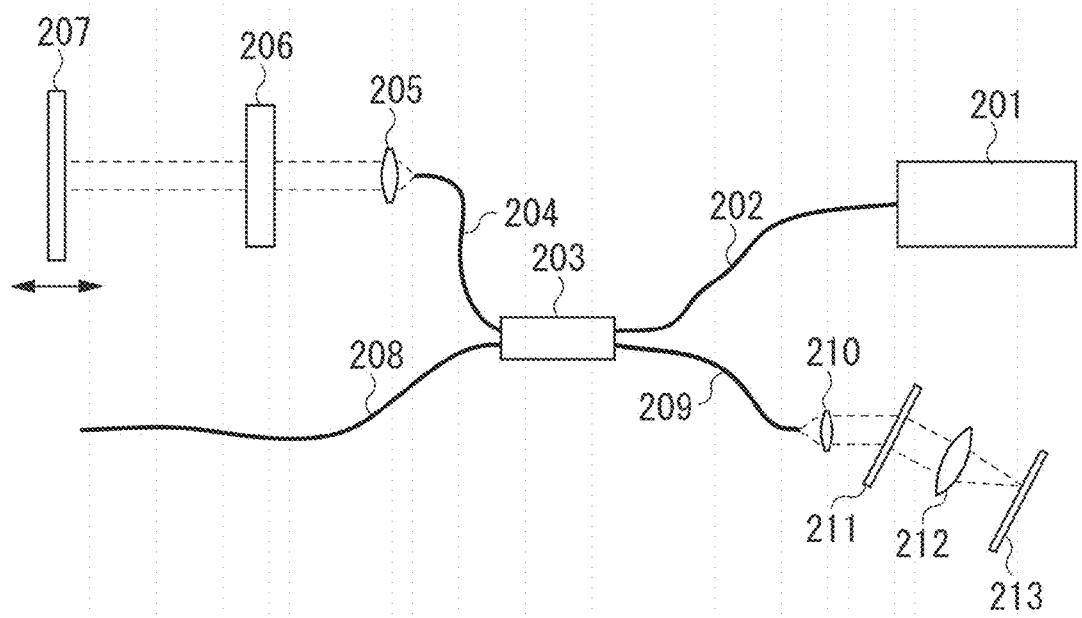
FIG. 2 is a block diagram illustrating a structure of an OCT unit.
Figure 3:
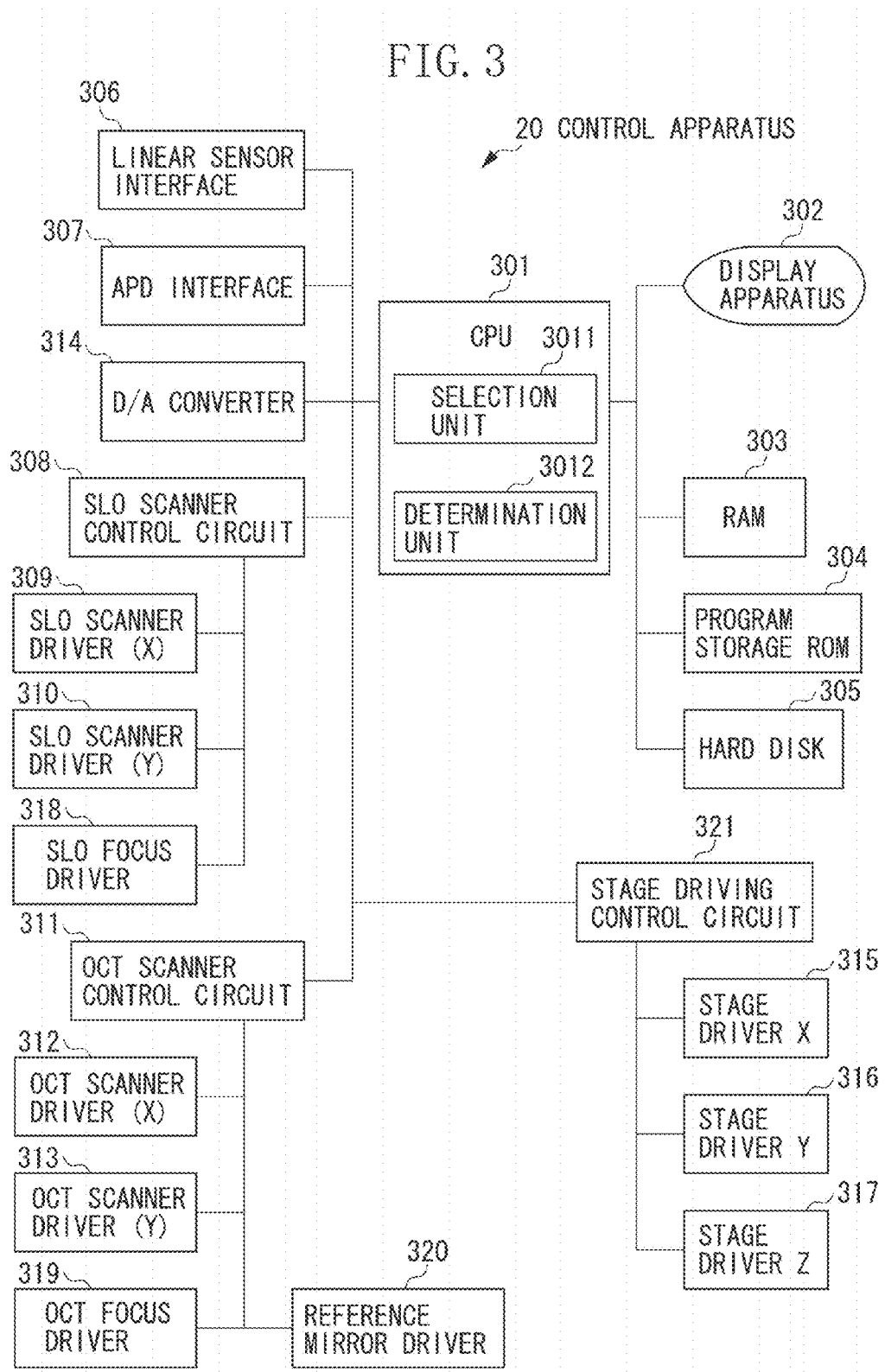
FIG. 3 is a block diagram illustrating a structure of a control apparatus.
Figure 4:
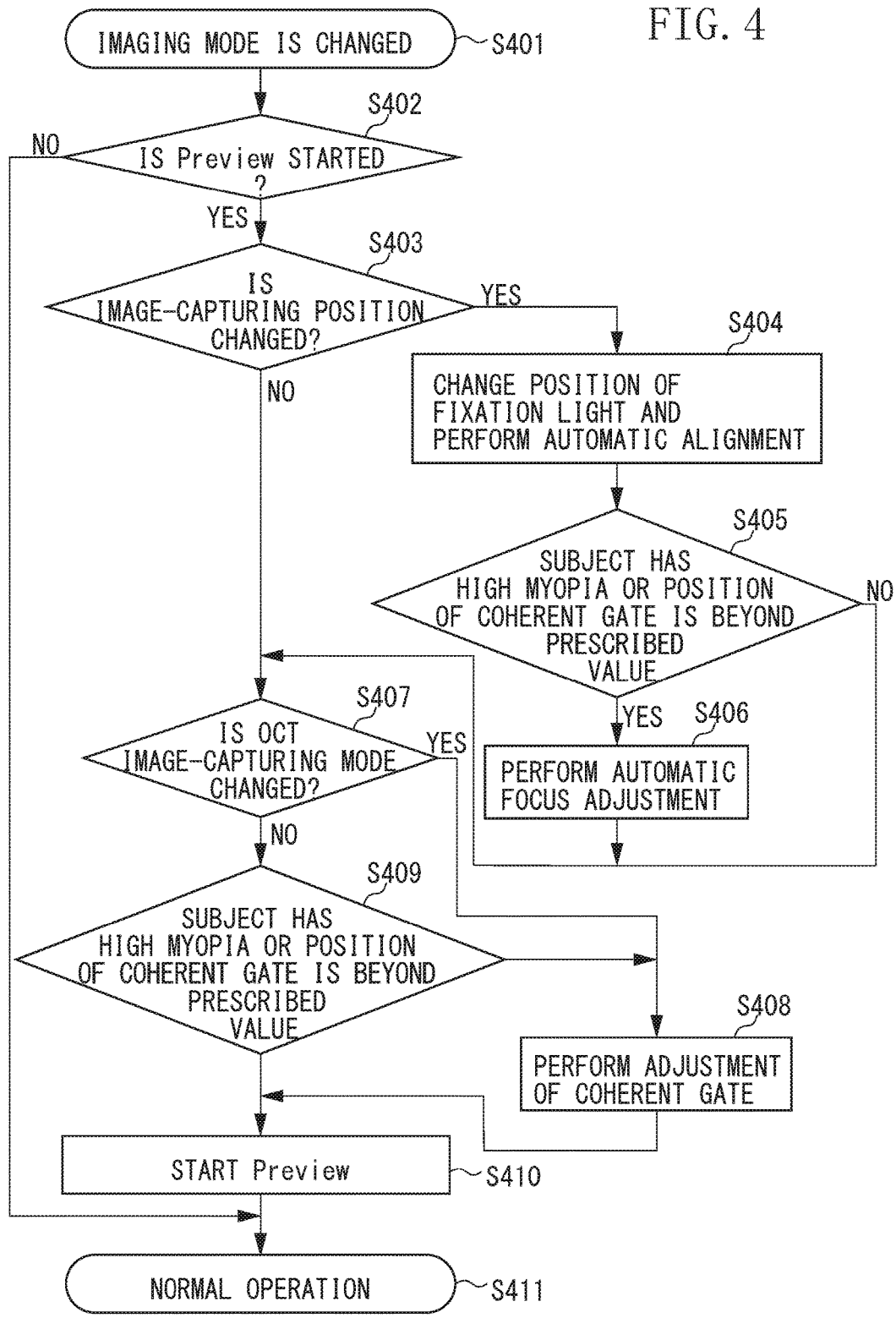
FIG. 4 is a flowchart illustrating a control process performed by a control apparatus.

FIG. 1 is an overall block diagram illustrating an image diagnosis system according to the present exemplary embodiment. FIG. 2 is a block diagram illustrating an OCT unit. FIG. 3 is a block diagram illustrating a control apparatus. FIG. 4 is a flowchart illustrating a control process performed by the control apparatus. The following exemplary embodiments are described with reference to these diagrams.

An image diagnosis system 1 according to the present embodiment includes an imaging apparatus 10 for checking a subject's eye portion, and a control apparatus 20 which performs image-capturing control processes on the imaging apparatus 10. The imaging apparatus 10 is an Optical tomographic apparatus that captures images of the fundus of a subject's eye based on the principle of Optical Coherence Tomography (OCT), and is provided with an optical tomographic unit, an anterior eye imaging unit configured to capture images of the anterior of a subject eye (herein referred to as the "anterior eye"), and an SLO image-capturing unit.

<Anterior Eye Imaging Unit>

With reference to FIG. 1, the anterior eye imaging unit is used for alignment, and the alignment performed therewith is described. A coordinate system of the present exemplary embodiment has its Z axis in the direction of a subject's eye axis, its X axis in the direction horizontal to a fundus image, and its Y axis in the direction perpendicular to the fundus image. The anterior eye is illuminated with a light emitting diode (LED) 120 for illuminating anterior eye. An image of the anterior eye is formed onto an anterior eye camera 119 using a beam splitter 116 and an anterior eye focus lens 117. The image is input into a central processing unit (CPU) 301 illustrated in FIG. 3.

<SLO, Fundus Imaging Unit>

With reference to FIG. 1, a Scanning Laser Ophthalmoscope (SLO) which is an apparatus for observing fundus is described. A laser light source 101 can be a semiconductor laser or a Super Luminescent Diode (SLD) light source. It is preferable to use a near-infrared wavelength range from 700 nm to 1000 nm, which decreases dazzle given to a subject during fundus observation, and maintains its high resolution. In the present exemplary embodiment, a semiconductor laser having a 780-nm wavelength is used, and the amount of the light of the laser can be changed using a control voltage.

A laser beam emitted from the laser light source 101 is converted into parallel light by a collimator lens 102, and passes through a hole of an aperture mirror 103, an SLO-X scanner 104, and an SLO-Y scanner 105. The beam further passes through a beam splitter 106, an eyepiece lens (objective lens) 107 and enters a subject's eye 108.

Hereinafter, a coordinate system of the present exemplary embodiment has its Z axis in the direction of a subject's eye axis, its X axis in the direction horizontal to a fundus image, and its Y axis in the direction perpendicular to the fundus image.

The beam incident on the subject's eye 108 is radiated on the fundus of the subject's eye 108 as a point beam of light. The beam is reflected or scattered by the fundus of the subject's eye 108 to return via the same optical path to the aperture mirror 103.

The reflected or scattered light beam is reflected by the aperture mirror 103 to be received by an avalanche photodiode (hereinafter, referred to as APD) 110 via an SLO focus lens 109, resulting in signals each representing the reflection and scattering intensity from a spot on the fundus. Then, raster scan by SLO scanners (X) and (Y) is achieved to obtain a two dimensional image of the fundus.

<OCT Unit>

An OCT unit 111 is described with reference to FIG. 2. The OCT unit 111 splits the low coherence light beam into a reference light beam and a signal light beam. The OCT unit 111 then combines the signal light beam returned from the subject's eye 108 and the reference light beam returned from the reference object to generate an interference light beam, which is subjected to color separation and output corresponding signals. The signals separated based on colors are input into the CPU 301. The CPU 301 analyzes the detected signals to form a tomographic image or a three dimensional image of the fundus.

The low coherence light source 201 includes a broadband light source emitting a low coherence light beam, and as the broadband light source in the present exemplary embodiment, a super luminescent diode (SLD) is used. The low coherence light beam includes a near-infrared range light, and also includes a coherent length of several tens micrometers, such as a light beam having a wavelength of about 800 nm to 900 nm.

The low coherence light beam emitted from the low coherence light source 201 is guided through an optical fiber 202 to an optical coupler 203. The optical fiber 202 is generally configured of a single mode fiber. The optical coupler 203 divide the low coherence light beam into a reference light beam and a signal light beam.

The reference light beam generated by the optical coupler 203 is guided through an optical fiber 204, and is converted into a parallel light flux by a collimator lens 205. The light flux passes through a glass block 206 which is a dispersion compensating unit configured to make the dispersion properties of the reference light beam and the observation light match each other. The light flux is then reflected by a reference mirror 207. The reflected reference light beam returns via the same optical path to enter the optical fiber 204.

The reference mirror 207 is movable in the travelling direction of the reference light beam. This structure enables adjustment of the path lengths of the reference light beam and an observation light beam caused by the eye axis length of the subject's eye 108 and a distance between the eyepiece lens (objective lens) 107 and the subject's eye 108.

The signal light generated by the optical coupler 203 passes through a fiber 208 to a scanner of the OCT and an eyepiece portion in FIG. 1. Then, the signal light is reflected and scattered by the retina of the subject's eye, and reenters the fiber 208. The signal light beam, which passes through the fiber 208 and guided into the optical coupler 203, is interfered with the reference light beam, and then passes through an optical fiber 209 to be converted into parallel light by a collimator lens 210. The parallel light is separated by a diffraction grating 211, and passes through an OCT focus lens 212 to form an image on one dimensional sensor 213.

The one dimensional sensor 213 may be a charge coupled device (CCD) sensor or a complementary metal oxide semiconductor (CMOS) sensor. The structure enables acquisition of signals from the one dimensional sensor 213 as separated signals of the interference light beam.

<OCT Scanning, Eyepiece Portion>

An OCT scanning mechanism is described with reference to FIG. 1. An OCT unit 111 emits a signal light. A collimator lens 112 converts the light into a parallel beam, which passes through an OCT-X scanner 113 and an OCT-Y scanner 114. The beam is reflected by a mirror 115 and the beam splitter 106 to pass through the eyepiece lens (objective lens) 107 into the subject's eye 108. The beam entered the subject's eye 108 is reflected and scattered by the fundus, as with the SLO, to return via the same optical path to the OCT unit 111.

<Control Unit>

The control apparatus 20 that controls the imaging apparatus 10 is described with reference to FIG. 3. A central processing unit (central processing unit (CPU)) 301 is connected to a display apparatus 302, a main storage apparatus 303 (random access memory (RAM)), and a storage apparatus 304 (read only memory (ROM)) that stores a program to execute the process in the flowchart in FIG. 4. The CPU 301 is further connected to a one dimensional sensor interface 306, an APD interface 307, and a digital to analog (D/A) converter 314.

The one dimensional sensor interface 306 receives data of the one dimensional sensor 213 as an output from the OCT. The APD interface 307 receives data of the APD as an output from the SLO. The D/A converter 314 generates a voltage for controlling the intensity of the SLO light source. The D/A converter 314 is connected to an SLO scanner control circuit 308 and an OCT scanner control circuit 311 (i.e., scanner controllers).

The control apparatus 20 controls operations for adjusting positions and settings of various members in the imaging apparatus 10. More specifically, the control apparatus 20 transmits commands to instruct adjustments together with control parameters of the adjustments to the imaging apparatus 10, so that the imaging apparatus 10 adjusts the positions and settings of various members thereof.

The SLO scanner control circuit 308 performs SLO scanner control using an SLO scanner driver (X) and an SLO scanner driver (Y), and controls the scan center position, the scan width, and the scan rate of the SLO scanner driver (Y), according to commands from the CPU 301.

The CPU 301 can acquire information about a scan position of an SLO beam from the SLO scanner control circuit 308. Similarly, the OCT scanner control circuit 311 performs OCT scanner control using the OCT scanner driver (X) and the OCT scanner driver (Y). The OCT scanner control circuit 311 controls the scan center position in the x and y directions, the scan widths in the x and y directions, and the scan rate, according to commands from the CPU 301. The CPU 301 can acquire information about a scan position of an OCT signal beam from OCT scanner control circuit 311.

A stage driving control circuit 321 can move a stage, which the apparatuses illustrated in FIGS. 1 and 2 are provided with, in the X, Y, and Z directions using a stage driver X 315, a stage driver Y 316, and a stage driver Z 317, respectively. The stage, which illustrated in FIGS. 1 and 2 are provided with, is mounted on a base (not illustrated), and the subject's eye, the stages, and the apparatuses mounted on the stages can be moved relative to the base.

The CPU 301 controls the apparatuses by executing a program stored in the program storage ROM 304 to perform the control process illustrated in the flowchart in FIG. 4. During the process, the CPU 301 serves as a selection unit 3011 and a determination unit 3012 by executing the program.

The selection unit 3011 selects an image-capturing mode according to a press-down of a button by a user. The "image-capturing mode" means an image capturing method defined by a combination of an image-capturing site and image-capturing conditions corresponding thereto. Thus, different image-capturing modes includes a case with different image-capturing conditions and different image-capturing sites, a case with the same image-capturing site and different image-capturing conditions, and a case with different image-capturing sites and the same image-capturing conditions.

The "image-capturing site of a subject's eye" refers to a tissue or an range of a subject's eye, such as a fundus, an anterior eye, a macula portion of a fundus, and an optic disc portion of a fundus.

In some cases, after a user presses a button to select an image-capturing mode, and adjustments are performed in the mode, another image-capturing mode is selected. Examples of such situations include a case where a user selects a correct image-capturing mode after accidentally selecting a wrong image-capturing mode, and a case where images of the same subject's eye are captured in a plurality of image-capturing modes.

In the above situations, the determination unit 3012 checks if the settings for adjustment items such as a coherence gate and an alignment are the same between image-capturing mode selected first (before changing) (first image-capturing mode), and the image-capturing mode selected next (after changing) (second image-capturing mode). The determination unit 3012 then sets the items that require no adjustment before and after the mode changing, and adjusts the items that do require adjustment.

The term used herein "Coherence Gate (CG)" refers to a position corresponding to the position of the reference mirror 207 on the reference optical path along the measuring path. If an imaginary optical path for the measuring beam reflected at the coherence gate position, the optical path has the same length as that of the optical path for the reference light beam reflected at the reference mirror.

For example, the determination unit 3012 determines whether to perform adjustment corresponding to a second image-capturing site, after the selection unit 3011 selects a first and second image-capturing sites and adjustment corresponding to the first image-capturing site is started, based on the first and second image-capturing sites. The determination unit 3012 also determines whether to perform adjustment corresponding to a second image-capturing site, when the second image-capturing site is input after adjustment corresponding to the first image-capturing site is started, based on the first and second image-capturing sites.

In a specific case, the CPU 301, the SLO scanner control circuit 308, the OCT scanner control circuit 311, or the stage driving control circuit 321 instructs both of adjustment of relative positions between a target object and the imaging apparatus 10 and adjustment of a coherence gate position.

The term "specific case" as used herein refers to a case where the position of a fixation light target, emitted from a light source of the imaging apparatus 10 for the first image-capturing site is different from that for the second image-capturing site. The term "target object" as used herein refers to a subject's eye. The term "first and second image-capturing sites" refer to different sites on the fundus of a subject's eye.

The determination unit 3012 determines to adjust the relative position of the imaging apparatus 10 to a subject' eye. When the first and second image-capturing site are on different layers of the retina of the subject's eye from each other, the determination unit 3012 determines to adjust a coherence gate position.

The CPU 301 perform control to adjust the items that are determined to be adjusted according to the determination made by the determination unit 3012. The term "alignment control" as used herein refers to an instruction from the CPU 301 to the stage driving control circuit 321 so that the stage is driven by a predetermined amount of distance.

<Alignment Control>

The alignment control can be performed by detecting a pupil from an image captured by an anterior eye camera, and driving the stages X and Y by the stage driving control circuit 321 so that the center of the pupil is positioned at the center of an image to be captured. The z direction of the stages can be adjusted by driving the stage by the stage driving control circuit 321 in the Y direction for focusing, using an image splitting prism 118 disposed near the lens 117.

<SLO process, Focus Adjustment>

An SLO image capturing process is described below. The CPU 301 sets a prescribed value to the D/A converter 314, and a predetermined center position for Y scanning, a scan speed, a scan width in the Y direction to the SLO scanner control circuit 308. With this, an SLO beam scans a retina. During the scanning, the APD outputs signals in proportion to the light intensity reflected and scattered from the retina. The SLO focus lens 109 is movable on the light axis by an SLO focus driver 318 for focusing.

The CPU 301 overlaps the intensity of the APD signal at the scanning positions respectively from the SLO scanner control circuit 308 to obtain an image of the retina. The image can be displayed by displaying it on the display apparatus 302.

The two dimensional image allows the operator to confirm a position to capture an OCT image. By performing control to maximize the contrast of the image, focusing can be performed.

The OCT focusing and the SLO focusing are performed through different optical systems. The driving of the optical systems is linked, and each focus position and a driving amount corresponding to the position are stored as table information in a hard disk 305. When the optical systems are driven based on the table information, the SLO focusing results in the OCT focusing.

<OCT Process, Coherence Gate Adjustment>

A process for OCT image capturing is described. The CPU 301 sets a center position in the x and y directions, a scan speed, a scan width in the x and y directions, and a main scan direction to the OCT scanner control circuit 311. With the set values, a signal light beam from the OCT unit 111 scans a retina.

During the scanning, the output from the one dimensional sensor 213 of the OCT unit 111 is input through the one dimensional sensor interface 306 into the CPU 301. The CPU 301 performs Fast Fourier Transformation (FFT) processing on the main storage apparatus 303 according to a program stored in the program storage ROM 304, and obtains information about the depth direction of the retina.

The depth direction information and the positional information from the OCT scanner control circuit 311 are used to obtain a B scan image, which is a cross-sectional image substantially parallel to the Z direction, and a three dimensional image of the retina. The images can be displayed by displaying them on the display apparatus 302.

The OCT focus lens 212 is movable along the optical axis by the OCT focus driver 319 for focusing. The reference mirror 207 is movable along the optical axis by the reference mirror driver 320. A position on a retina corresponding to the reference mirror 207 is referred to a coherence gate, and a portion closer to the coherence gate provides an image having a higher intensity.

Figure 5:
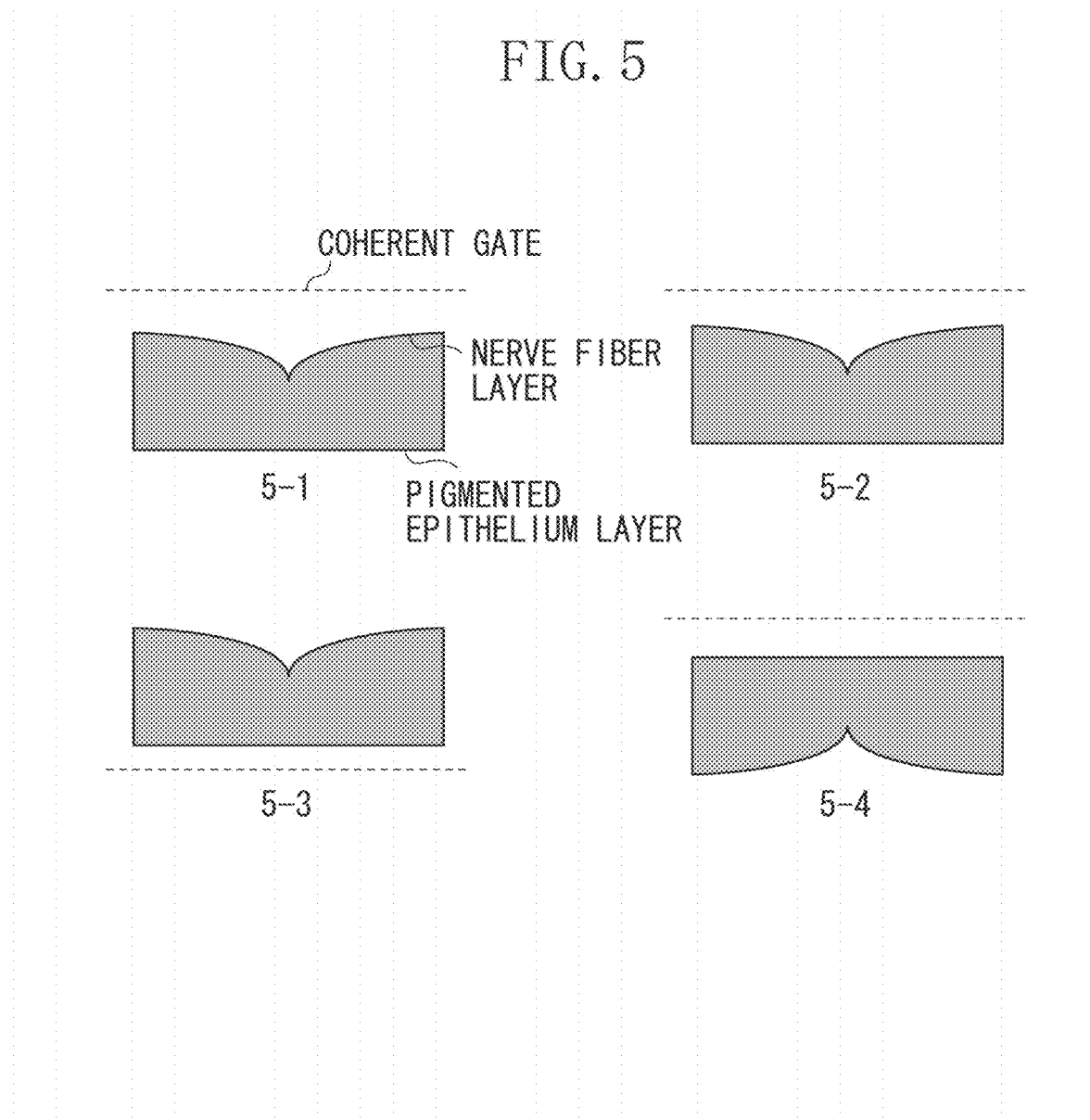
FIG. 5 is a view illustrating the positional relationship between a coherence gate position and an OCT tomographic image.

With reference to FIG. 5, the positional relationship between a coherence gate position and a resultant OCT tomographic image is described. A coherence gate located at an upper portion of a retina as illustrated in an image 5-1 results in capturing of an image 5-2. In this case, the nerve fiber layer of the eye is more clearly imaged than the pigmented epithelium layer, and therefore image capturing in this case is suitable for observation of the upper portion of a retina, for checking glaucoma for example. The observation mode is herein referred to as a vitreous body mode.

A coherence gate located at a lower portion of a retina as illustrated in an image 5-3 results in capturing of an upside-down image as an illustrated in an image 5-4. This is because the OCT measures the distance from the coherence gate. In this case, the pigmented epithelium layer is more clearly imaged than the nerve fiber layer, and image capturing in this case is suitable for observation of the lower portion of a retina, for checking macula lutea degeneration, for example. The observation mode is herein referred to as a choroid membrane mode. Apparently, in this mode also, an image is displayed upside down with the upper portion of a retina being disposed on the upper side of the image.

In the vitreous body mode, a coherence gate is automatically adjusted by positioning a coherence gate sufficiently far from a retina, generally in a vitreous body of the eye, and approaching the coherence gate gradually to the retina to find a position where the retina image appears and an image of the entire retina can be captured. In the choroid membrane mode, on the contrary, a coherence gate is automatically adjusted by positioning a coherence gate below a retina on a choroidal side, and approaching the coherence gate gradually to the retina to find a position where a retina image appears and an image of the entire retina can be captured.

The above operations lead to automatic adjustment of a coherence gate.

<Operations>

Figure 6:
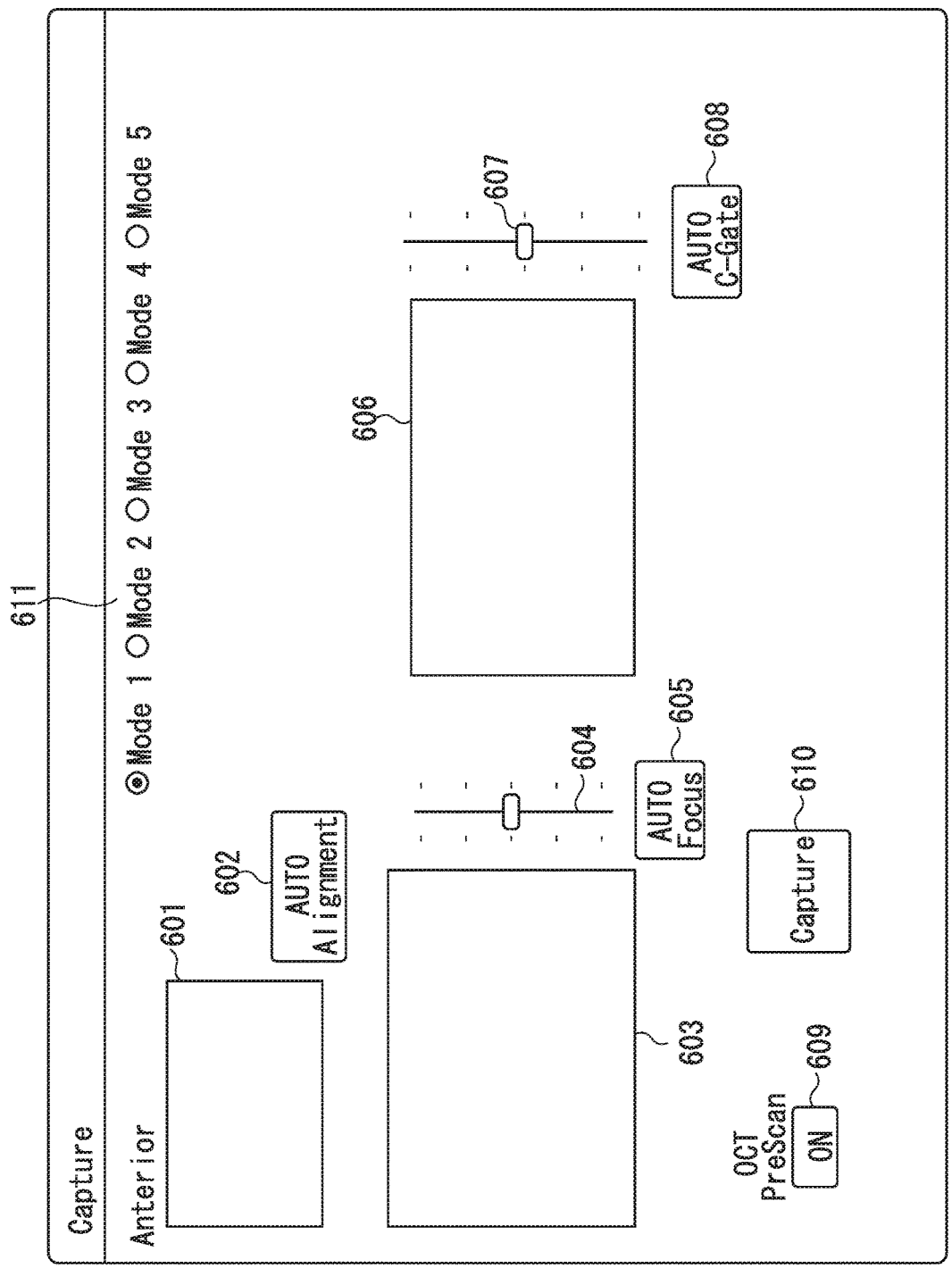
FIG. 6 is a view illustrating an example of an operation screen displayed on a display apparatus 302.

FIG. 6 illustrates an example of an operation screen displayed on the display apparatus 302. In FIG. 6, the operation screen includes an anterior eye image 601, a start button 602 for automatic alignment adjustment, a fundus image 603 captured by SLO, and a scroll bar 604 for manual focus adjustment. The operation screen further includes an automatic focus adjustment start button 605, a retina tomogram 606 captured by OCT, and a scroll bar 609 for manual coherence gate adjustment. The operation screen further includes an automatic focus start button 608, a prescanning start button 609, an OCT image capturing button 610, and an image-capturing mode changing button 611.

With respect to the image-capturing mode, the following items can be specified in advance: a scan pattern such as a one dimensional image and a two dimensional image, a scan position to determine a position of a fixation light such as at a macula portion and at an optic disc portion, and an OCT image-capturing mode such as the vitreous body mode and the choroid membrane mode of a coherence gate.

In the above operation screen, when a subject places his/her eye in front of the apparatus, only the anterior eye image 601 is displayed, and the fundus image 603 and the retina tomogram 606 are not displayed. When the prescanning start button 609 is pressed, an automatic alignment adjustment is performed, and then SLO and OCT image capturing are started, so that the fundus image 603 and the retina tomogram 606 are displayed. At this time, other adjustments are not performed, so that the images are not displayed correctly.

Subsequently, an automatic focus adjustment and a subsequent automatic coherence gate adjustment are performed, so that the fundus image 603 and the retina tomogram 606 are displayed in correctly adjusted states.

If determining that the images are correctly displayed, the operator presses the OCT image capturing button 610 to perform OCT image capturing. If determining that focusing and/or coherence gate adjustment are not correctly performed, the operator uses the corresponding scroll bars respectively for manual adjustments.

After the OCT image capturing button 610 is pressed for OCT image capturing and before an OCT image is captured, if an operator wants to change the current image-capturing mode, there may be a case where readjustments need to be performed on some items. In the present exemplary embodiment, based on the image-capturing modes before and after the mode change, the determination unit 3012 determines the items, and performs automatic adjustments on the items only.

The above operation is described with reference to a flowchart illustrated in FIG. 4. In step S401, the image-capturing mode changing button 611 is pressed, and the selection unit 3011 selects an image-capturing mode, so that the image-capturing modes are changed. In step S402, the determination unit 3012 determines whether a preview is performed or not. If a preview is not performed (NO in step S402), in step S411, the process ends and a normal operation starts.

If a preview is started (YES in step S402), a fixation light is changed to a position suitable for an image-capturing site in response to the mode change. At this time, the eye may have moved, which requires readjustment of alignment. Therefore, in step S403, it is determined whether the image capturing position is changed. If it is determined that the image capturing position is changed (YES in step S403), the processing proceeds to step S404. In step S404, the CPU 301 as a control unit performs automatic alignment adjustment. If it is determined that the image capturing position is not changed (NO in step S403), the processing proceeds to step S407.

When the subject has high myopia, the fundus is likely to be aspherical. This causes a difference in distances from the objective lens to the macula and to the optic disc, for example. Thus, the visual acuity of the subject can be input in advance to the apparatus, so that the information is used to determine whether there is a difference in the distances.

In other cases, if the coherence gate is at a position beyond a prescribed value, the subject is likely to have axial myopia which is accompanied by a longer eye axis than normal. Accordingly, in step S405, the determination unit 3012 determines that the subject has axial myopia (YES in step S405), and in step S406, the CPU 301 performs automatic focus adjustment.

In step S407, the determination unit 3012 determines whether the OCT image-capturing mode is changed between the vitreous body mode and the choroid membrane mode. When the mode is changed (YES in step S407), in step S408, the CPU 301 performs adjustment of the coherence gate.

In step S409, the determination unit 3012 determines whether the subject has high myopia or whether the coherence gate is at a position beyond a prescribed value, as in step S405. When it is determined that the subject has high myopia (YES in step S409), adjustment of the coherence gate is required for the same reason, and thereby in step S408, the CPU 301 similarly performs adjustment of the coherence gate.

In step S408, the positional information of the retina is already obtained, and thereby adjustment can be completed more quickly than the case described in the <OCT Process, Coherence Gate Adjustment>.

Since, a human retina has a constant thickness of 1 mm or less not depending on individuals. Accordingly, for example, when the image-capturing mode is changed from the vitreous body mode to the choroid membrane mode, the coherence gate is moved by about 1 mm away from the retina to perform the above adjustment, which results in a quicker adjustment.

Through the above processing, an automatic adjustment that is required due to mode change only is automatically executed when image-capturing modes are changed, and thereby image capturing can be performed appropriately and in a short period of time in the changed image-capturing mode.

The above processing is useful because the period of time for adjustment can be reduced, especially when the coherence gate and alignment are once returned to their reference positions respectively before coherence gate adjustment and alignment adjustment are performed.

The above processing is also useful in cases where the preprocess for image capturing adjustment and the other processes performed before adjustment take a long time before mirrors, lenses, and stages are moved. For example, when a focus adjustment is performed in a known hill-climbing method, unless a focus lens is driven, the CPU 301 cannot determine whether the focus is appropriate or not.

On the contrary, in the present exemplary embodiment, when determination unit 3012 determines that there is no change in a focus position accompanied by the change of the image-capturing mode, the focus adjustment itself through driving of a focus lens becomes unnecessary. Consequently, the period of time required for adjustment before imaging can be reduced.

In the above exemplary embodiment, the image-capturing modes are changed after a preview image capturing and before a main image capturing. Alternatively, an image of the same subject's eye may be subsequently captured in another image-capturing mode after the main image capturing is performed.

In a second exemplary embodiment, an image-capturing method for capturing images of an eye in a shortest period of time by determining the order of the image-capturing modes, when tomograms of a subject's eye are to be obtained in a plurality of image-capturing modes, is described.

The block diagrams of entire system, the OCT unit 111, and the control unit of the present exemplary embodiment are the same as those illustrated in FIGS. 1 to 3 respectively, therefore descriptions thereof are omitted. In the present exemplary embodiment, there are two or more image-capturing modes. In the present exemplary embodiment, to one image-capturing site, only one image-capturing mode is set, and therefore the image-capturing conditions are different for the different image capturing modes.

The imaging apparatus 10, when capturing images of preselected image-capturing sites in a predetermined order, obtains images of the image-capturing sites respectively by performing adjustment corresponding to one image-capturing site, capturing an image of the image-capturing site, changing setting for another image-capturing site, and repeating these operations in this order for each site.

When a plurality of image-capturing sites are selected, the CPU 301 of the control apparatus 20 controls the order of the image-capturing sites for image capturing, according to a determination result by the determination unit 3012, so that the period of time for adjustment of the imaging apparatus 10 is minimized.

The adjustment items in the imaging apparatus 10 for each of the image-capturing sites can respectively have fixed standard periods of time required for adjustment. Accordingly, a storage unit in the imaging apparatus 10 stores table information containing the adjustment periods of time in an organized manner for the adjustment items.

The determination unit 3012 then uses the table information to determine the order of the image-capturing sites for imaging so that the adjustment period of time is optimized. The order of the image-capturing sites for imaging is determined by calculating the total period of time required for adjustment for each of the permutations of the selected image-capturing sites, and selecting the permutation requiring the shortest period for adjustment as the order for imaging.

The CPU 301 determines whether adjustment is required, for any order for imaging, in response to a change of an image-capturing site. The adjustment includes shifting between right and left eyes, alignment adjustment, focus adjustment, and coherence gate adjustment. The determination is made based on the image-capturing conditions that are related to the image-capturing sites before and after the change.

Figure 7:
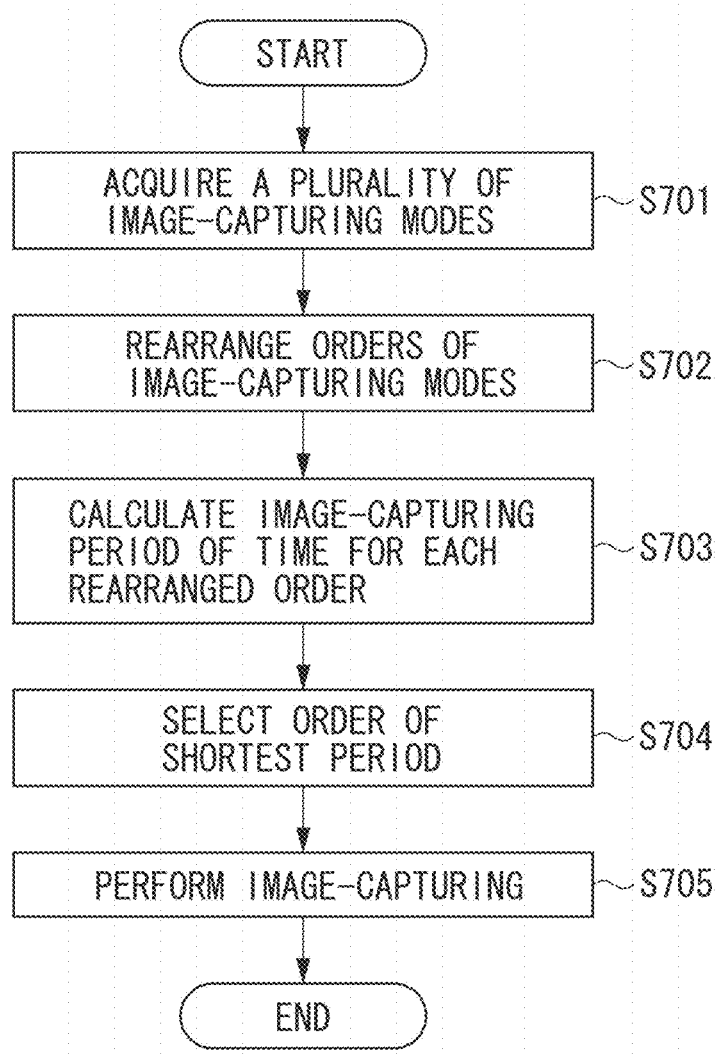
FIG. 7 is a flowchart illustrating another control process according to an exemplary embodiment.

With reference to the flowchart in FIG. 7, a specific procedure performed by the control unit of the present exemplary embodiment is described. In step S701, the selection unit 3011 obtains instructions for a plurality of modes for image capturing of a subject's eye, in response to a press down of the image-capturing mode changing button 611 by an operator (not illustrated).

In step S702, the CPU 301 functioning as a control unit calculates all of the rearranged orders of the instructed image-capturing modes. At the calculation, the determination unit 3012 determines whether shifting between right and left eyes, alignment adjustment, focus adjustment, and coherence gate adjustment are individually required at each of the mode changing. The determination is made based on a table described below.

In step S703, the CPU 301 functioning as a control unit calculates a period of time required for imaging throughout each of the rearranged orders of the instructed image-capturing modes. In step S704, the CPU 301 functioning as a control unit selects the order calculated as requiring the shortest period for imaging in step S703. In step S705, the CPU 301 functioning as a control unit executes an image capturing of a subject's eye in the order of the image-capturing modes selected in step S704.

The above process is described using an example. In the present exemplary embodiment, the OCT apparatus provides the image-capturing modes illustrated in FIG. 8.

As illustrated in FIG. 8, in each of the image-capturing modes, a position of a fixation light and a coherence gate mode are associated to each other as items of image-capturing conditions. In the present exemplary embodiment, the periods of time required for adjustments before imaging are illustrated in FIG. 9.

As illustrated in step S701, an operator selects one of the image-capturing modes 1 to 4 illustrated in FIG. 10. The processing in step S702 is then executed. The image-capturing modes are then rearranged, and the period of time for imaging in each rearranged order of the image-capturing modes is calculated.

FIG. 11 illustrates all of the rearranged orders of the instructed image-capturing modes. FIG. 11 also illustrates which adjustments are necessary for the image capturing in each order. In other words, even when an adjustment is necessary in a mode for imaging, if the adjustment was already executed in the previous mode, the adjustment does not have to be repeated. In FIG. 11, each adjustment item has "○" if readjustment is necessary, and "X" if readjustment is not necessary.

Shifting between right and left eyes: when another eye is specified for image capturing, the optical head of the imaging apparatus 10 needs to be shifted between right and left eyes.

Change of fixation light position: for each image-capturing mode, the fixation light position is predetermined. In the present exemplary embodiment, the fixation light is positioned differently in a macula mode and an optic disc mode.

Anterior eye alignment adjustment: when the optical head of the imaging apparatus 10 is moved, an alignment of the anterior eye is required. When the position of a fixation light is changed, another alignment of the anterior eye is required because the eyeball moves.

Fundus focus adjustment: when the optical head of the imaging apparatus 10 is moved, fundus focus adjustment is required. Alternatively, when the position of a fixation light is changed, another alignment of the anterior eye is required because the eyeball moves.

Coherence gate adjustment: when the optical head of the imaging apparatus 10 is moved, coherence gate adjustment (CG adjustment) is required. Alternatively, when the position of a fixation light is changed, coherence gate alignment is required because the eyeball moves. Alternatively, even when a coherence gate mode necessary for the image-capturing mode is changed (e.g., from the vitreous body mode to the choroid membrane mode, or vice versa), coherence gate adjustment is required.

Based on the above rule, the results in FIG. 11 are obtained.

The process in step S703 is performed next. As illustrated in FIG. 12, the number of times adjustment is required are sorted in each order of image capturing. The total period of time required for adjustment is calculated for each order of image capturing, according to FIG. 9, FIG. 11, and the following formula. The calculated adjustment periods of time are listed in the rightmost column in FIG. 12.

Calculated adjustment period of time=the number of times of shifting between right and left eyes*period of time required for shifting between right and left eyes+the number of times of alignments*period of time required for alignments+the number of times of focus adjustments*period of time required for focus adjustments+the number of times of CG adjustments*a period of time required for CG adjustments The process in step S704 is performed next. FIG. 12 indicates that the order 3-4-1-2 requires the shortest period of time, and that the order requires 111 seconds. The process in step S705 is performed next. Image capturing is performed in the order of mode 3, mode 4, mode 1, and mode 2.

The control apparatus 20 stores the tables illustrated in FIGS. 8 to 12 in the ROM 304 or the hard disk 305, so that the above control is executed using the information in the tables. As described above in the present exemplary embodiment, when images of a subject's eye are captured in a plurality of image-capturing modes, the order of the image-capturing modes is rearranged to minimize the readjustment period of time to be required, which enables image capturing of the eye within a short period of time.

When the period of time for adjustment changes depending on the amount of adjustment, the period of time for adjustment is estimated in view of the amount of adjustment, so that the calculation for the period becomes more accurate. This can also reduce the period of time for adjustment.

In addition, when the period of time for adjustment changes depending on the amount of adjustment or where the period of time for adjustment cannot be estimated accurately, for reduction in the period of time required for the process to control the order of image capturing, the order of image capturing is determined so that the number of times of adjustments is minimized, instead of the period of time for adjustments. This can reduce the period of time required for the process to control the order of image capturing.

When changing the image-capturing modes, elimination of necessary adjustment may be effective, but at the same time complete elimination of adjustments for some items may result in inappropriate image capturing. In a third exemplary embodiment, in view of above possibility, a rough adjustment control and other specific adjustment control are not performed based on the image-capturing modes before and after the changing.

Figure 13:
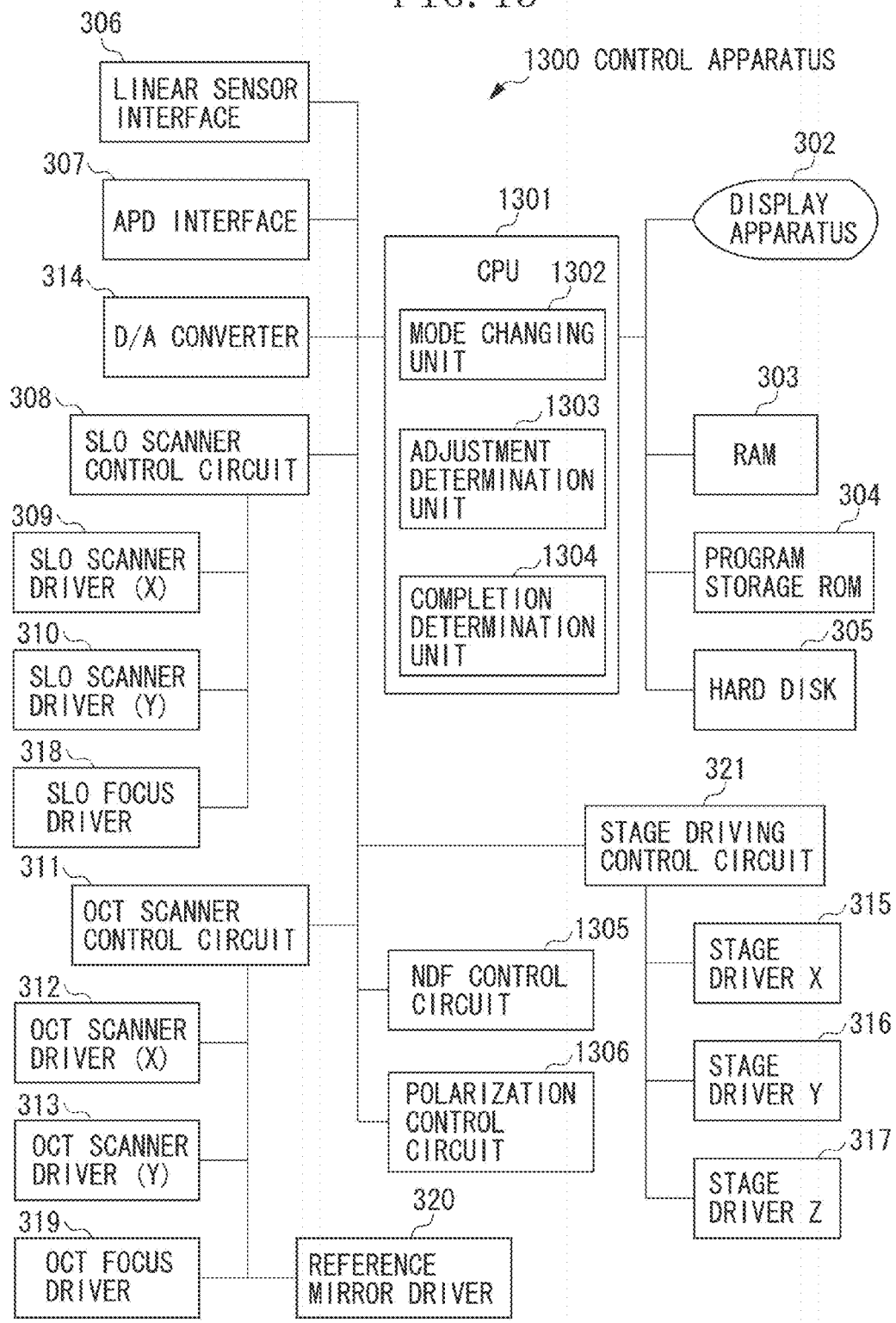
FIG. 13 is a view illustrating a structure of a control apparatus according to a third exemplary embodiment.

FIG. 13 illustrates a control apparatus according to the present exemplary embodiment. The configurations of the OCT image-capturing unit, the SLO image-capturing unit, and other components similar to those of the above exemplary embodiment are not described.

A CPU 1301 of a control apparatus 1300 integrally controls the processes performed by the control apparatus 1300. The CPU 1301 loads programs from the ROM 304 onto the RAM 303 to perform the processes illustrated in the flowcharts in FIGS. 14, 15, 16, 18, and 19, and executes commands contained in the programs. Accordingly, the CPU 1301 functions as a mode changing unit 1302, an adjustment determination unit 1303, and a completion determination unit 1304.

The mode changing unit 1302 changes image-capturing modes. The adjustment determination unit 1303 determines whether to perform adjustment for each item, in response to the mode change. The completion determination unit 1304 determines whether the adjustments are completed, and whether the condition is ready to obtain an appropriate image.

The control apparatus 1300 includes an neutral density filter (NDF) control circuit 1305 that rotates an NDF placed in a reference optical path to control the intensity of a reference light beam. The control apparatus 1300 further includes a polarization control circuit 1306 for controlling the polarization states of a measuring beam and the reference light beam that are combined by the optical coupler 203.

Figure 14:
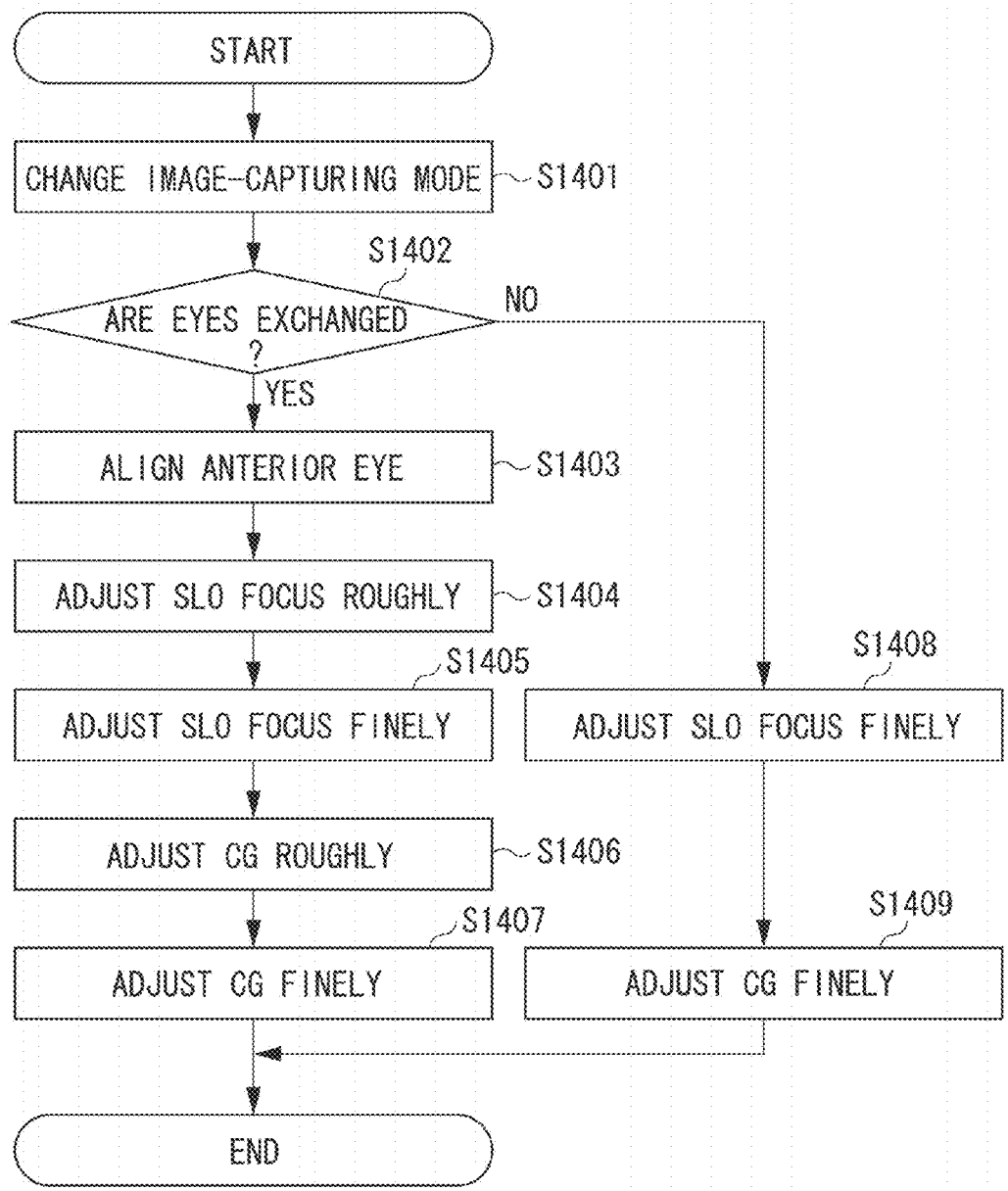
FIG. 14 is a flowchart illustrating a control in changing image-capturing modes.

According to a flowchart illustrating in FIG. 14, a process performed by the control apparatus 1300 having the above structure is described. In the processing illustrated in FIG. 14, the CPU 1301 skips rough adjustment depending on the situation. In a different standpoint, the adjustment determination unit 1303 determines the size of a searching range for adjustment by the imaging apparatus 10, according to whether a target eye of a subject is changed or not.

In step S1401, the mode changing unit 1302 changes image-capturing modes in response to an input from an operation unit such as a mouse, a keyboard, or a touch panel device (not illustrated). For example, when an image-capturing mode different from the current image-capturing mode is selected through a graphical user interface (GUI) screen illustrated in FIG. 6, in response to an instruction given by press-down of an image-capturing mode changing button 611, the mode changing unit 1302 changes the image-capturing modes.

The image-capturing modes are defined in association with a set of image-capturing parameters, as in the above exemplary embodiments. The parameters include information about right and left eyes, a fundus alignment position, a coherence gate position, and a focus position.

In step S1402, the adjustment determination unit 1303 refers to the image-capturing mode information before and after the changing that is stored in the memory, to determine whether the target eye is changed. The "change of eyes" means the target eye for image capturing is changed to another one due to changing between right and left eye of a subject or changing of subjects. When the adjustment determination unit 1303 determines that the target eye is changed (YES in step S1402), the process proceeds to step S1403.

In step S1403, the stage driving control circuit 321 performs alignment of an anterior eye. The alignment of an anterior eye is performed by moving the stage by the stage driving control circuit 321, and positioning a target eye onto an optical path of an image capturing optical system of the apparatus 10.

In step S1404, the SLO scanner control circuit 308 performs rough adjustment of an SLO focus. In the focus rough adjustment, the SLO scanner control circuit 308 moves a focus position using the focus driver 318 at a predetermined pitch (i.e., a first focus pitch) within the entire range where the focus position is changeable or a predetermined range (i.e., a first focus range).

At each focus position, the SLO scanner control circuit 308 captures images of the fundus of a subject's eye, and detects contrast of the obtained images. The position giving the highest contrast image is identified as a roughly adjusted position, which ends the rough adjustment. The specified position is stored in the RAM 303.

In step S1405, the SLO scanner control circuit 308 performs fine adjustment of the SLO focus. In the focus fine adjustment, the SLO scanner control circuit 308 refers to the roughly adjusted position stored in the RAM 303, and moves a focus position at a predetermined pitch (i.e., a second focus pitch) within a predetermined range (i.e., a second focus range) around the roughly adjusted position.

The second focus range is narrower than the first focus range, and the second focus pitch is smaller than the first focus pitch. The position giving the highest contrast in the SLO image that is obtained by shifting a focus at the second focus pitch is identified as a finely adjusted position, which ends the fine adjustment. The identified position is stored in the RAM 303 and the hard disk 305.

In the present exemplary embodiment, the imaging apparatus 10 in FIG. 1 has only one focus lens, but may have focus lenses in the SLO and the OCT respectively. A plurality of focus lenses provides an advantage in solving the problem that the angle of field of the OCT and the pupil position are changed along with movement of the SLO focus.

In this case, an OCT focus position can be appropriately set interlocking with an SLO focus position. More specifically, concentration of the light from the SLO light source onto a fundus can be achieved through an appropriate setting of an OCT focus position using the information of the light source such as wavelength.

The CG adjustment after the SLO focus adjustment provides an appropriate tomographic image. In other words, in a case where an OCT focus adjustment is performed previously, if coherence gate adjustment has not been performed appropriately at the point of time, no tomographic image is obtained.

Even when a coherence gate position has been appropriately set, if the focus position of the OCT light source is not appropriate at the point of time, the interference light beam is weakened, resulting in no tomographic image. An SLO image can be obtained if it is only in focus. Therefore, after the focus adjustment is performed for an SLO image and the OCT focus adjustment is performed interlocking therewith, then the CG adjustment is performed in this order. Thus, an appropriate OCT tomographic image can be efficiently obtained.

In step S1406, the OCT scanner control circuit 311 performs rough adjustment of a coherence gate (CG). In the CG rough adjustment, the OCT scanner control circuit 311 moves a CG position using the reference mirror driver 320 at a predetermined pitch (i.e., a first CG pitch) within the entire range where the CG position is movable or a predetermined range (i.e., a first CG range).

At each CG position, the OCT scanner control circuit 311 captures a tomographic image of the fundus of a subject's eye, and determines the luminance value of the obtained tomographic image. The position giving the tomographic image of a retina is identified as a roughly adjusted CG position, which ends the rough adjustment.

The determination whether a tomographic image of a retina is obtained or not is made using the pixel value (luminance value) of the tomographic image. If tomographic images are obtained at a plurality of CG positions respectively, the CG position having the largest pixel value is identified as the roughly adjusted position. The identified CG position is stored in the RAM 303.

In step S1407, the OCT scanner control circuit 311 performs fine adjustment of an OCT coherence gate (CG). In the CG fine adjustment, the OCT scanner control circuit 311 refers to the roughly adjusted CG position stored in the RAM 303, and moves the CG position at a predetermined pitch (i.e., a second CG pitch) within a predetermined range (i.e., a second CG range) around the roughly adjusted CG position.

The second CG range is narrower than the first CG range, and the second CG pitch is smaller than the first CG pitch. The position giving the tomographic image having the largest luminance value that is obtained by shifting the CG at the second focus pitch is identified as a finely adjusted CG position, which ends the fine adjustment. The identified position is stored in the RAM 303 and the hard disk 305.

In contrast, in step S1402, when it is determined that the target eye is not changed (NO in step S1402), in step S1408, the SLO scanner control circuit 308 performs fine adjustment of the SLO focus as in step S1405. In step S1409, the OCT scanner control circuit 311 performs fine adjustment of the coherence gate (CG) as in step S1407.

When images of the same eye are captured in different image-capturing modes in serial, anterior eye alignment, SLO focus fine adjustment, and CG rough adjustment can be omitted. With this, efficiency in adjustments when image-capturing mode is changed is improved, and thereby cycle time for image capturing can be improved.

On the other hand, even if the rough adjustment is omitted, since significant change does not occur in alignment and focus of the anterior eye portion because it is the same eye, only with the fine adjustment, the adjustment can be performed accurately.

Figure 15:
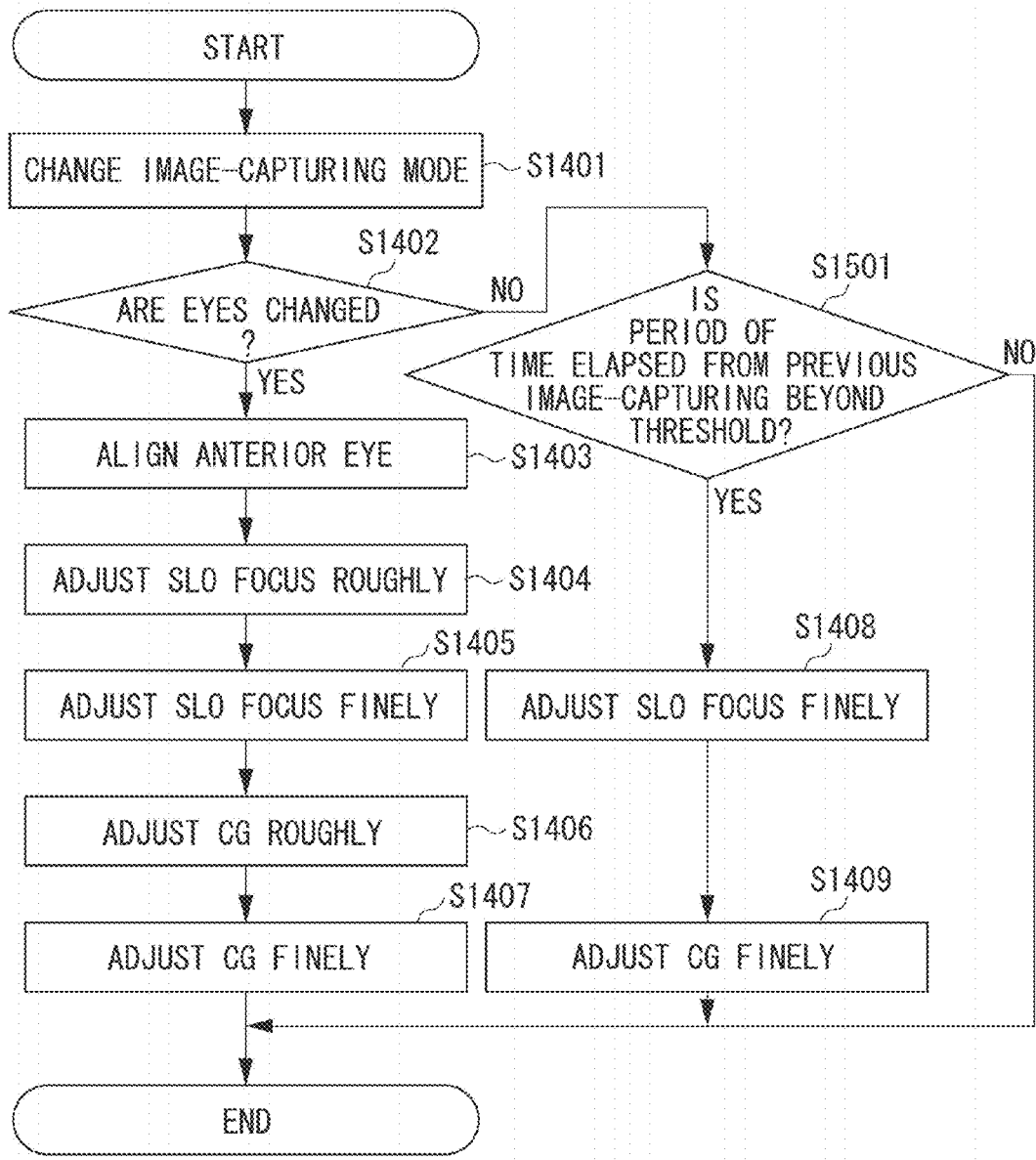
FIG. 15 is a flowchart illustrating a process to change adjustment control according to a time interval between image capturing.

Even if the image-capturing modes are changed, when only a short period of time has elapsed since the previous imaging, the situation almost remains the same, and thereby the fine adjustment can be omitted. FIG. 15 illustrates a flowchart of adjustment control corresponding to such a situation.

According to the flowchart illustrated in FIG. 15, a process performed by the control apparatus 1300 having the above structure is described. The processing similar to that in FIG. 14 is not described.

The CPU 1301 measures period of time elapsed from a previous image capturing, using a clock. In step S1501, the adjustment determination unit 1303 obtains an elapsed time t from a previous image capturing. The adjustment determination unit 1303 also obtains a time t threshold from the hard disk 305 as a threshold. The time t threshold may have a prescribed value or may be changeable by an operation from a user through the operation unit.

The adjustment determination unit 1303 compares the elapsed time t with the time t threshold. When the adjustment determination unit 1303 determines that the elapsed time t is larger than the time t threshold (YES in step S1501), the processing proceeds to step S1408. When the adjustment determination unit 1303 determines the elapsed time t is not larger than the time t threshold (NO in step S1501), the CPU 1301 skips steps S1408 and S1409, and ends the process.

When the image capturing interval is very short as described above, both of the rough adjustment and the fine adjustment can be omitted, further reducing the cycle time for image capturing.

In the process illustrated in FIG. 15, the fine adjustment is omitted depending on the image capturing interval length, but, for example, the adjustment determination unit 1303 may determine whether to omit the fine adjustment or not according to the information set by the user and stored in the memory. In this case, the user can control adjustment, as the user desires.

Figure 16:
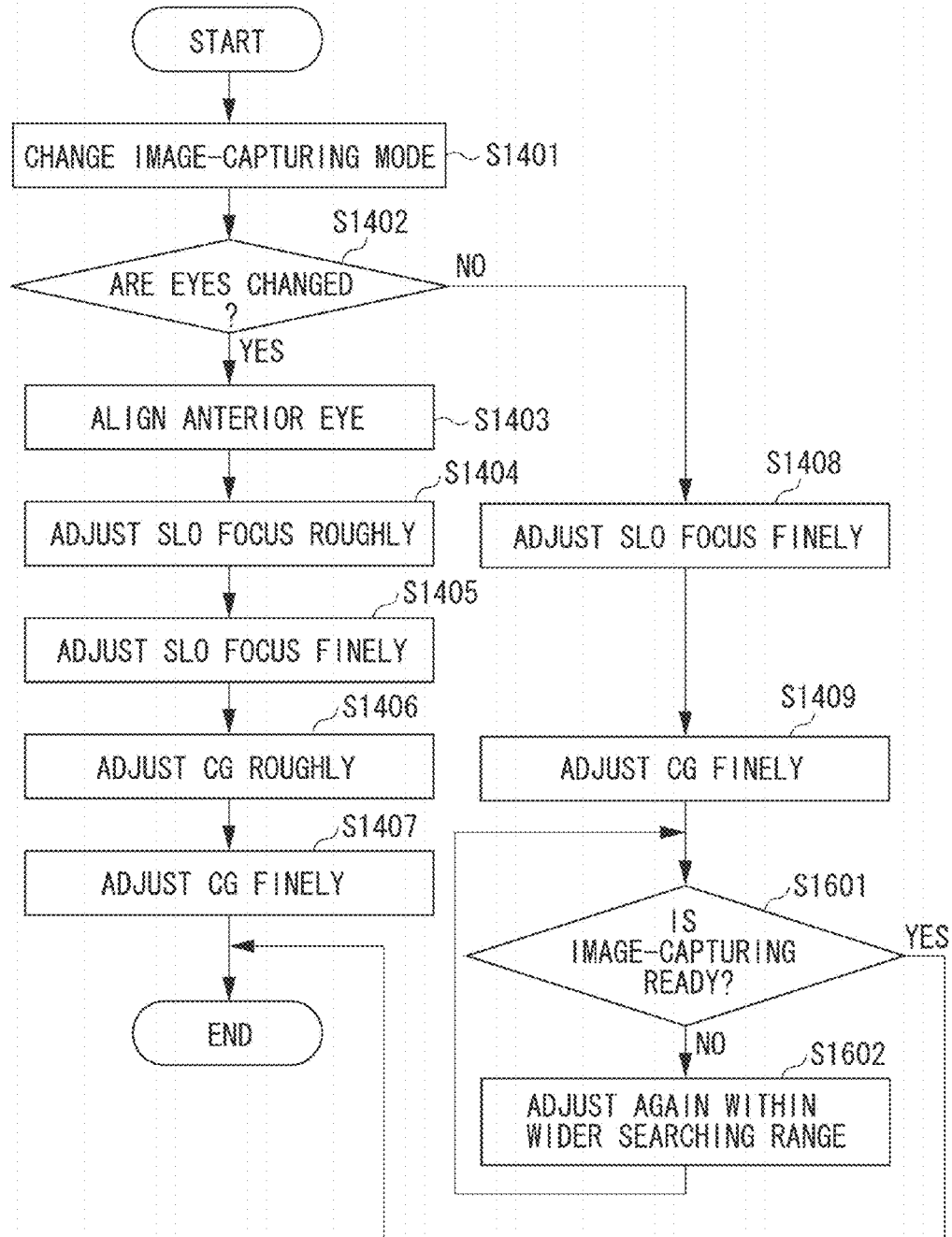
FIG. 16 is a flowchart illustrating a process for readjustment that is continued until completion of adjustment.

When the rough adjustment is omitted after changing the image-capturing modes, adjustment may be sometimes insufficient due to movement of a subject for example. FIG. 16 illustrates a flowchart of adjustment control corresponding to such a situation.

According to the flowchart illustrated in FIG. 16, a process performed by the control apparatus 1300 having the above-described structure is described. The processing similar to that illustrated in FIG. 14 is not described.

In step S1601, the completion determination unit 1304 determines whether adjustment is completed and whether image capturing can be started. The determination is made by checking the luminance value and/or image quality of an obtained tomographic image, and determining whether the luminance value and/or image quality meets predetermined criteria. The completion determination unit 1304 also determines whether the resultant tomographic image contains a retina therein, using the luminance value. When the image of the retina is not contained therein (NO in step S1601), the completion determination unit 1304 determines that adjustment is not completed.

In step S1602, the CPU 1301 performs readjustment of the focus and the coherence gate. The readjustment is performed within a third focus range and a third CG range that are wider than the second focus range and the second CG range, respectively.

As described above, when it is determined that more adjustment is necessary after the fine adjustment, readjustment is performed within a wider searching range than that for the fine adjustment, thereby leading to an appropriate adjustment. The adjustment range can be expanded until sufficient readjustment is performed. Accordingly, when only one readjustment is not enough, readjustment can be repeated until no more adjustment is necessary.

when it is determined that more adjustment is still necessary after adjustment was performed within the range for rough adjustment illustrated in steps S1404 to S1407, a notification indicating criteria satisfying image cannot be obtained is displayed on the display unit 302, which can omit useless repetition of adjustments.

When it is determined that more adjustment is necessary even after readjustments were performed within the expanded predetermined range, the readjustment may be ended after the readjustment is repeated within the predetermined range for a predetermined period of time, even if the adjustment fails due to accidental events such as movement of a subject, without any adjustment performed within a needless range.

Figure 17:
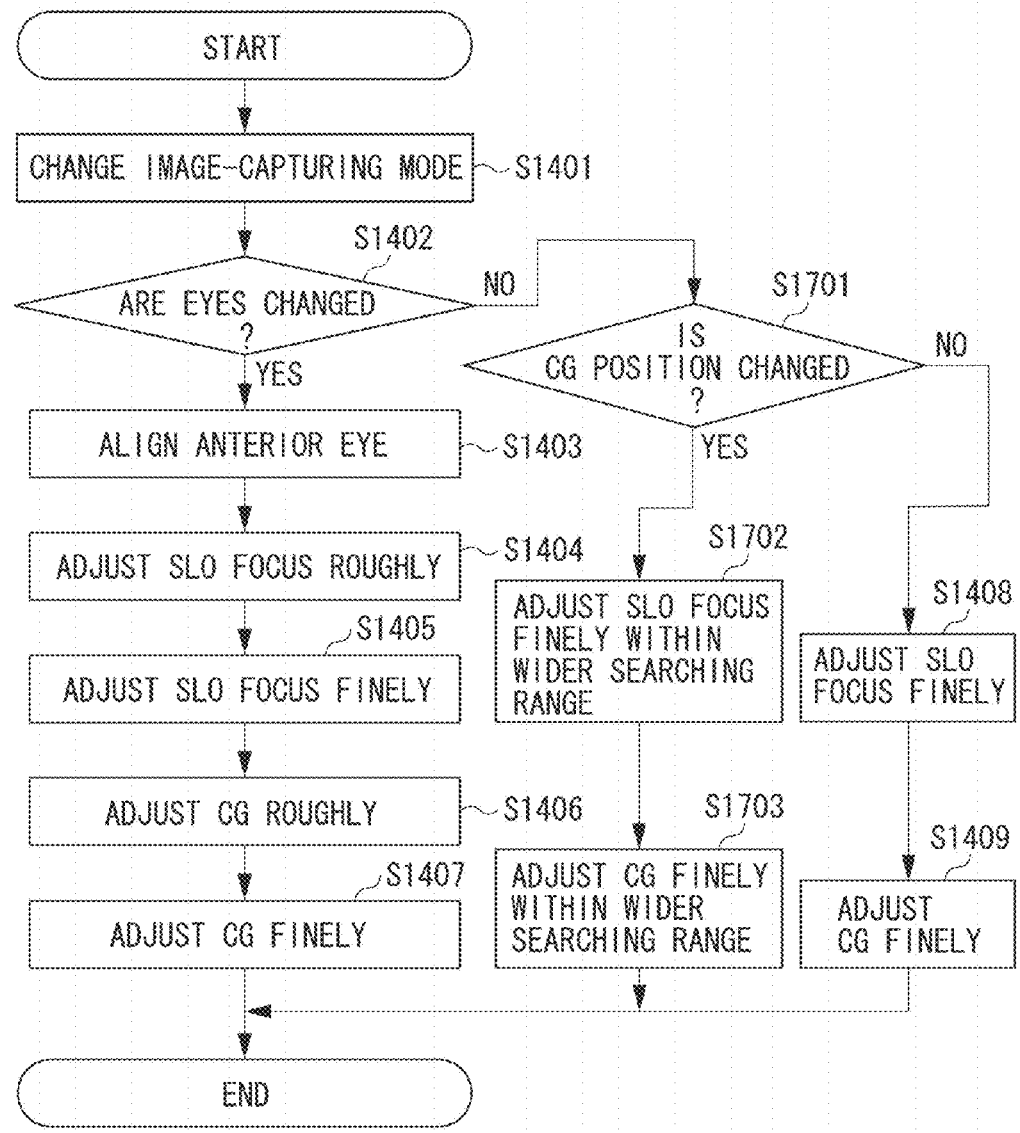
FIG. 17 is a flowchart illustrating a process to change adjustment control according to change in coherence gate.

If the coherence gate position is changed, sometimes fine adjustment may be needed within a wider range than that for the case without change in the coherence gate position. FIG. 17 illustrates a flowchart for adjustment control corresponding to such a situation.

According to the flowchart in FIG. 17, a process performed by the control apparatus 1300 having the above-described structure is described. The processing similar to that illustrated in FIG. 14 is not described.

In step S1701, the adjustment determination unit 1303 refers to the information of the image-capturing modes before and after changing that is stored in the hard disk 305, and determines whether the CG position has been changed. Examples of the CG position mode include a vitreous body mode in which the CG is set on the vitreous body side at the distance equal to that from the reference optical path, and a choroid membrane mode in which the CG is set on the choroidal side.

When adjustment determination unit 1303 determines that the CG position has not been changed (NO in step S1701), as illustrated in FIG. 14, the fine adjustments in steps S1408 and S1409 are performed. When determining that the CG position has been changed (YES in step S1701), the adjustment determination unit 1303 determines more adjustment is needed within a wider range, and the processing proceeds to step S1702.

The focus position adjustment in step S1702 is performed within a searching range different from that in step S1408. The SLO scanner control circuit 308 sets the focus adjustment range as a third focus range smaller than the first focus range and larger than the second focus range. In other words, the adjustment in step S1702 is performed within a range wider than that for the fine adjustment in step S1408.

The adjustment in step S1702 may be performed by moving a focus at a second focus pitch, but a third focus pitch may be used which is smaller than the first focus pitch and larger than the second focus pitch, so that the increase in the period of time for adjustment can be suppressed.

The CG position adjustment in step S1703 is performed within a searching range different from that in step S1409. The OCT scanner control circuit 311 sets the CG adjustment range as a third CG range which is smaller than the first CG range and larger than the second CG range. In other words, the CG adjustment in step S1703 is performed within a range wider than that for the fine adjustment in step S1408.

In step S1703, the CG or focus searching range (i.e., the third CG range or the third focus range) may be determined, according to the change content for a target position in an adjustment item set in the imaging apparatus 10.

Figure 18:
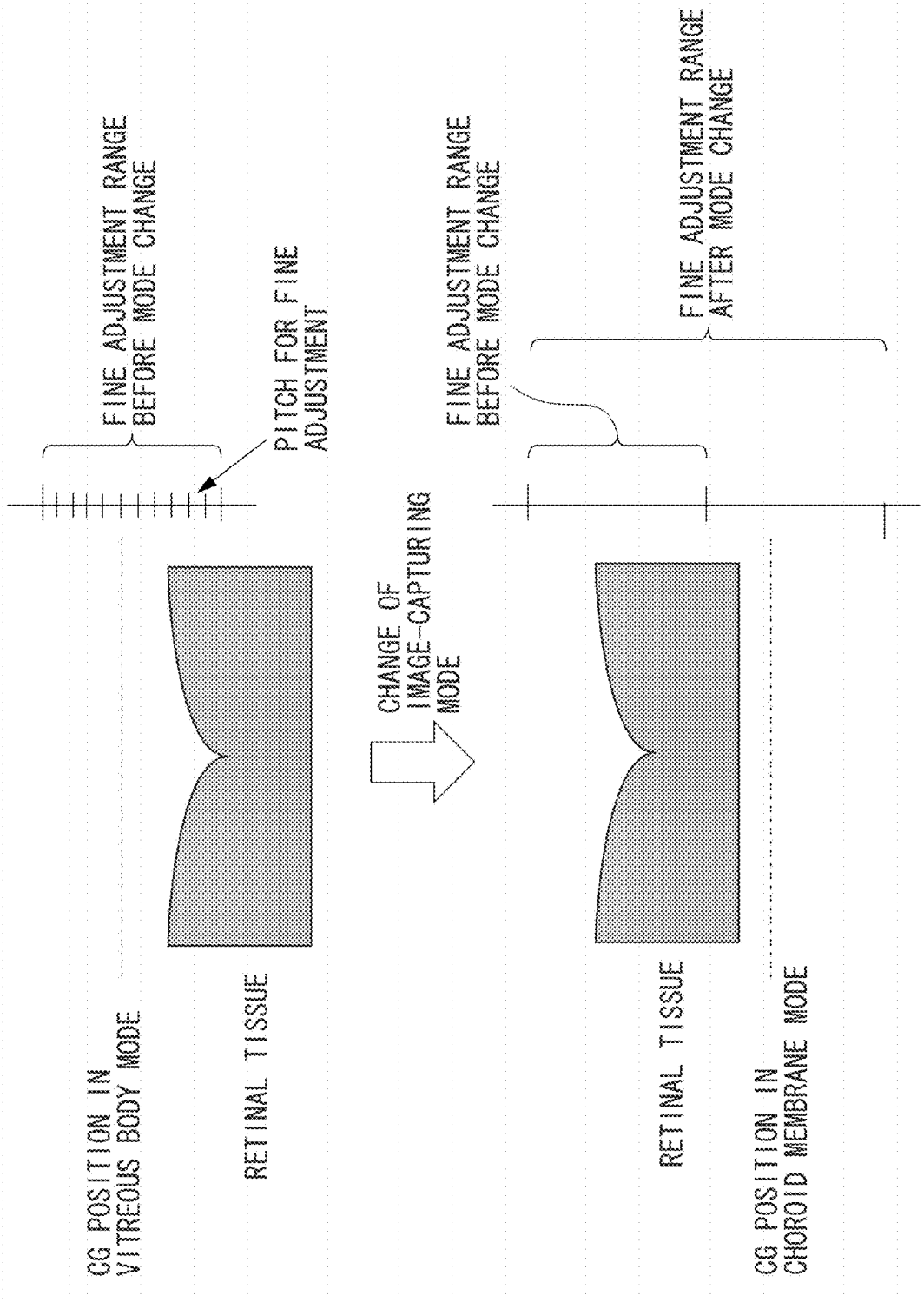
FIG. 18 is a view illustrating a range used for coherence gate fine adjustment after changing the image-capturing modes.

With reference to FIG. 18, fine adjustment of a coherence gate after changing of the image-capturing modes in step S1703 in FIG. 17 is described. FIG. 18 illustrates a case where the CG position is changed from the vitreous body mode to the CG position in the choroid membrane mode.

In the upper portion of FIG. 18, an adjustment range (i.e., the second range) in the vitreous body mode (before changing of the image-capturing mode), and a pitch (i.e., the second pitch) are illustrated. In the lower portion of FIG. 18, the searching range is extended in the depth direction of the eye because it is the change from the vitreous body mode to the choroid membrane mode.

As illustrated in FIG. 18, the change of a coherence gate position includes a direction. Therefore, the adjustment determination unit 1303 specifies the changed direction based on the image-capturing modes before and after the changing, and sets the third CG range to be extended in the specified direction.

In this way, efficient setting of a CG position can be achieved. With respect to a focus position also, the same concept can be used. The adjustment determination unit 1303 determines a third focus range as a focus searching range, leading to efficient setting of a focus position.

In the adjustment in step S1703, the pitch in CG movement may be the second CG pitch, but a third CG pitch that is narrower than the first CG pitch and wider than the second CG pitch may be used, which further can suppress the increase in adjustment period of time for adjustment.

As described above, depending on the information about mode changing, an adjustment range can be adaptively-changed to achieve both of reduction in cycle time for image capturing and maintenance of image quality. In the present exemplary embodiment, when a CG position is changed due to mode changing, adjustment is performed within a searching range wider than that for fine adjustment in FIG. 14. This extension leads to a tomographic image having a better quality, even when the coherence gate is changed, by performing an appropriate adjustment with a reduced period of time.

Figure 19:
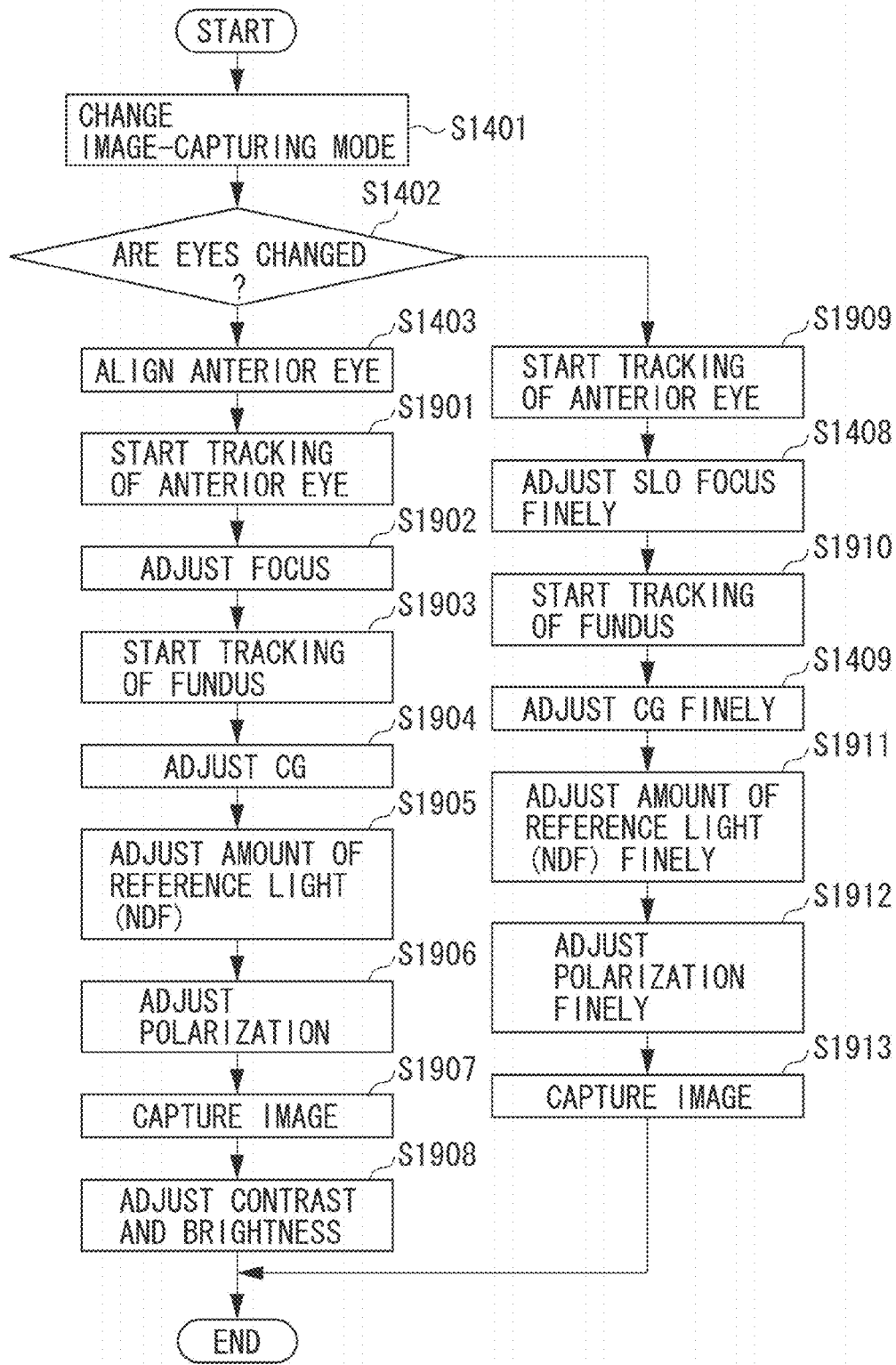
FIG. 19 is a flowchart illustrating another control in changing the image-capturing modes.

The items for the adjustment are not limited to those illustrated in FIGS. 14 to 18. FIG. 19 illustrates a flowchart of a control process with an increased number of items.

According to the flowchart in FIG. 19, a process performed by the control apparatus 1300 having the above-described structure is described. The processing similar to that in FIG. 14 is not described.

In step S1901, the stage driving control circuit 321 performs tracking of an anterior eye. An anterior eye imaging unit captures images of the anterior eye at a predetermined frame rate. The anterior eye imaging unit calculates differences between frames to identify motion vectors over the images, so that the stage is moved in the direction of the motion vectors. These operations are repeated to maintain alignment with the anterior eye.

In step S1902, the SLO scanner control circuit 308 specifies a focus position through a known hill-climbing method that uses contrast detection. The image used for the detection is an SLO image.

In step S1903, the SLO scanner control circuit 308 starts tracking of a fundus. The eye continuously is moving due to small involuntary eye movement, fixation disparity, and movement of the subject. Due to the affect of the movements, sometimes the setting of a coherence gate may take a longer time, or cannot be performed appropriately.

TO avoid the affect, SLO images are captured at a predetermined frame rate with a focus being on the fundus, and differences between the frames are obtained to specify motion vectors in the SLO images. The OCT scanner control circuit 311 is then controlled so that the scan position of the OCT scanner is moved by the identified motion vectors.

In step S1904, the OCT scanner control circuit 311 performs coherence gate adjustment. In the adjustment, as described above, a CG position is sequentially moved within the first CG range. When a tomographic image of a retina can be obtained by moving the CG position, the adjustment range is narrowed after obtaining thereof, and more accurate adjustment is performed. The CG position giving a maximum pixel value of the image is stored as an adjusted CG position into the hard disk 305.

In step S1905, the NDF control circuit 1305 rotates a neutral density filter (NDF) placed in a reference optical path to control the intensity of a reference light beam.

The NDF is of a disk shape, and has attenuation coefficients that are different depending on the positions thereon substantially in a continuous manner along the circumferential direction. Rotation of such NDF by a motor changes the attenuation coefficient of the light passing therethrough. The NDF control circuit 1305 rotates the NDF to produce a maximum luminance value so that the intensity of the reference light beam and the intensity of the measuring beam are maintained at an appropriate ratio.

In step S1906, the polarization control circuit 1306 controls a polarization state of the measuring beam and the reference light beam that are combined by the optical coupler 203. The polarization control circuit 1306 changes and controls the polarization states of the reference light beam and the interference light beam respectively to obtain an appropriate interference light beam at the optical fiber 203. By using the luminance value of an image obtained by the interference light beam, the polarization state is adjusted to be an appropriate state.

In step S1907, the CPU 1301 automatically instructs to start capturing of tomographic images of a subject's eye, in response to an instruction for imaging from a user or completion of the adjustments. The operations for image capturing have been described in the first exemplary embodiment, which are not described here.

In step S1908, the CPU 1301 controls contrast and brightness. When a 20-bit image was obtained in the image capturing in step S1907 for example, the CPU 1301 performs a process to convert the 20-bit image into an 8-bit image. In the conversion, the CPU 1301 obtains a histogram of the image to specify a minimum value and a maximum value thereof. The maximum value may be the average of the pixel values of the top 1%, and the minimum value may be the average of the pixel values of the bottom 1%.

The pixel value range defined by the maximum and minimum values is divided into 256 gradations (8 bits) to obtain images. Such setting provides an image with appropriate contrast and brightness.

In step S1909, the SLO scanner control circuit 308 starts tracking of an anterior eye, as in step S1902. The tracking corresponds to the fine adjustment in anterior eye alignment, and is necessary even if the target eye is not changed.

In step S1910, the SLO scanner control circuit 308 performs tracking of a fundus, as in step S1903. The tracking enables appropriate image capturing even when a subject's eye cannot be see the fixation light in a fixed manner due to its movement. In other words, the tracking serves as a process for fine adjustment of alignment.

In step S1911, the NDF control circuit 1305 performs fine adjustment of an amount of the reference light beam. In the fine adjustment, the NDF is rotated within a range narrower than the searching range in step S1905, based on the amount of the reference light beam stored in the hard disk 305, to obtain an amount of the reference light beam as a suboptimal value.

In step S1912, the polarization control circuit 1306 performs fine adjustment of a polarization state. In the fine adjustment, the polarization state is changed within a range narrower than the searching range in step S1906, based on the polarization state stored in the hard disk 305, to set the polarization state to a suboptimal state.

In step S1913, the CPU 1301 instructs to start capturing of tomographic images of a subject's eye, as in step S1907.

As described above, the adjustment of an amount of the reference light beam, the adjustment of a polarization state, and the adjustment of contrast and brightness after image capturing may be omitted depending on a situation.

When the focus adjustment or the hill-climbing method using contrast detection is used, adjustment range can be narrowed to set a start position for adjustment based on the information about the previous image capturing, the adjustment can be performed efficiently. The same advantage can be obtained for the other adjustment items.

In a third exemplary embodiment, the following case may also occur in that after a first image-capturing mode is set, adjustment corresponding to the image-capturing mode is started, and then the image-capturing mode is changed before completion of the adjustment.

In this case, the adjustment determination unit 1303 of the control apparatus 1300 determines on a target eye exchange in step S1402, and also determines to which step the process for the adjustment has progressed in FIG. 14, for example.

If the target eye has not been exchanged and steps S1403 and S1404 are being performed or are completed, the processing of step S1405 and the subsequent steps is continued. This is because uncompleted rough adjustment needs to be finished.

When an image-capturing mode is changed during the focus fine adjustment in step S1405 or after the completion of the focus fine adjustment, the CPU 1301 instructs the SLO scanner control circuit 308 to repeat the focus fine adjustment in step S1405. The processing of step S1406 and the subsequent steps is continued. This is because the focus rough adjustment has been completed, and only fine adjustment is necessary.

When an image-capturing mode is changed during the CG rough adjustment in step S1406, the fine adjustments in step S1408 and step S1409 are performed after completion of the CG rough adjustment. When an image-capturing mode is changed after completion of the CG rough adjustment in step S1407, the processing of step S1408 and the subsequent steps is continued.

The above operations prevents repetition of the rough adjustment, leading to efficient adjustment processing.

When the processing of step S1408 or step S1409 is being performed, the CPU 1301 instructs the SLO scanner control circuit 308 and the OCT scanner control circuit 311 to perform the focus fine adjustment and CG fine adjustment respectively again.

If the target eye has been changed, no matter which step is being performed, the processing proceeds to step S1403, and processing thereafter is continued.

In the above exemplary embodiments, the SLO focusing and the CG adjustment may be performed in parallel. For example, when the SLO and the OCT individually have a focus lens, the OCT focus can be adjusted using the OCT focus driver 319 of the OCT scanner control circuit 311, in conjunction with the SLO focus adjustment.

At the same time, the OCT scanner control circuit 311 uses an OCT scanner driver (X) 312 and an OCT scanner driver (Y) 313 for OCT scanning to obtain a tomographic image, and performs CD adjustment by moving the reference mirror using the reference mirror driver 320 according to the information of the resultant image. This decreases the period of time for adjustment.

Furthermore, at the point of time when the SLO focus rough adjustment in step S1404 and the OCT focus rough adjustment being in conjunction with the rough adjustment in step S1404 are completed, the SLO focus fine adjustment in step S1405, the CG rough adjustment in step S1406, and the CG fine adjustment in S1407 are performed in parallel. With these adjustments, when the OCT focus is roughly obtained, a coherence gate adjustment can be performed efficiently using the information of the tomographic image.

Similarly, the SLO focus fine adjustment in step S1408, OCT focus fine adjustment being in conjunction with the fine adjustment in step S1408, and the CG fine adjustment in step S1409 are performed in parallel, leading to reduction in the period of time for adjustment.

In the third exemplary embodiment, when the eye is exchanged, the searching range is extended and adjustments are repeated from a rough adjustment. However, it is not limited thereto, and when it is known that the right and left eyes have similar characteristics, the rough adjustment may be omitted, even when the target eye is changed. In this case, however, alignment of an anterior eye needs to be performed again.

In the above exemplary embodiments, the first to third exemplary embodiments are described independently, but it is not limited thereto, and these exemplary embodiments can be combined. For example, the CPU 1301, after determining the existence of high myopia or misalignment of the coherence gate performed in step S405 of the first exemplary embodiment, issues instruction to perform focus rough adjustment of coherence gate rough adjustment even when the eye is not exchanged. In this way, appropriate adjustment can be performed in a case of high myopia or coherence gate misalignment.

In addition, for example, when the programmed image capturing is performed as in the second exemplary embodiment, the period of time required for rough adjustment and fine adjustment is measured in advance. The measured period of time is stored in the hard disk 305, so that the order of image capturing is determined in view of the period of time, leading to more efficient image capturing.

In the first exemplary embodiment, it is determined whether adjustment is required for each adjustment item according to the change of the image-capturing mode (or the image-capturing site) after capturing the preview. In the second exemplary embodiment, it is determined whether adjustment is required for each adjustment item according to the shift of the image-capturing mode (or change of the image-capturing site), the image-capturing modes (or exchange of the image-capturing sites) being set before image capturing.

However, it is not limited thereto, and for example, a case may occur in which an image-capturing mode (or an image-capturing site) is set, and the image-capturing mode is changed after adjustment corresponding to the image-capturing site is started and the adjustment is completed. In one exemplary embodiment, in such a case, the table illustrated in the second exemplary embodiment may be used to determine whether readjustment is required or not for each adjustment item, and the adjustment is performed only for the items requiring the adjustment.

Similarly, the determination process by the determination unit 3012 and adjustment control by the CPU 301 serving as a control unit can be performed, even after completion of adjustment and before completion of preview image capturing.

In the first exemplary embodiment, the determination unit 3012 may not make a determination on a coherence gate position when it is determined that the position of the fixation light is different before and after changing of the image-capturing modes as the image-capturing conditions.

Instead, both adjustment of the relative positions of the test object and the imaging apparatus (alignment adjustment), and the adjustment of the coherence gate position may be performed. Different alignments means different sites to be imaged, and thereby even if both sites reside near the choroid membrane in their depth directions, sometimes a coherence gate cannot be aligned with the choroid membrane for the different sites.

As another example, in the second exemplary embodiment, the CPU 301 determines the optimal order of image capturing according to the input image-capturing modes (or the image-capturing sites), displays the optimal order on the display apparatus 302. When receiving a signal indicating a user's permission of the image capturing in the order, the CPU 301 starts image capturing in the determined order.

Furthermore, a user may desire to instruct a specific order of image capturing, for example, when a user desires to determine whether image capturing of other sites are to be performed or not according to the result of a previously captured images of a specific image-capturing site. For such a case, a user can instruct changing of the determined order of image capturing through a keyboard and mouse (not illustrated), for example.

The CPU 301 serving as a control unit changes the order of image capturing in response to the instruction, and controls image capturing to be performed in the changed order.

When a user sets a restriction to the order of image capturing, the CPU 301 may be configured to determine the order of image capturing so that the period of time required for image capturing is minimized in the restriction. In this case, the CPU 301 serves as a determination unit configured to determine the order of image capturing and a display control unit for the display apparatus 302.

The imaging apparatus may be provided with both functions of the first and second exemplary embodiments. In this case, the CPU 301 may determine whether to execute each function according to a selection from a user.

The above exemplary embodiments are described on the assumption that the imaging apparatus has an automatic adjustment function. However, in the imaging apparatus without the automatic adjustment function, and in which adjustment is performed manually, the imaging apparatus may notify a user of necessary adjustment items and unnecessary adjustment items.

In this case, the determination unit 3012 determines whether adjustment for each item is necessary or not before and after changing of image-capturing modes, and the CPU 301 causes the display apparatus 302 to display the determination results. In this way, an operator inexperienced to the OCT imaging apparatus can perform settings of image capturing efficiently, and the burden to the subject can be reduced because the period of time required for image capturing is reduced.

In the above exemplary embodiments, the control apparatus 20 is separated from the imaging apparatus 10, but the imaging apparatus 10 may include the control functions of the control apparatus 20.

The control according to the above exemplary embodiments can be applied to an imaging apparatus that captures images of a biological object or an object to be examined other than an eye portion. The application of the control to an OCT imaging apparatus using the principle of Optical Coherence Tomography results in reduction in period of time required for alignment.

When the above-described control is applied to an OCT imaging apparatus for eye examination, a subject's head may be fixed to the imaging apparatus 10 during adjustment and image capturing to reduce the burden of the subject who needs to hold fixation to the fixation light.

The above-described control may be applied to an image capturing system or image diagnosis system whose functions are shared with a plurality of apparatuses.

An embodiment of the present invention also includes a computer program to realize the functions and processes performed in the above exemplary embodiments.

When the program reads and executes a program, the functions according to the exemplary embodiments are achieved. Alternatively, the functions according to the exemplary embodiments may be achieved in cooperation with an operation system (OS) running on a computer based on instructions from the program. In this case, the OS partly or entirely executes the actual processes, and the functions according to the exemplary embodiments can be achieved.

The above exemplary embodiments are only examples, and embodiments of the present invention is not limited to those exemplary embodiments.

Another embodiment of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within an embodiment of the present invention.

While the present disclosure has been described with reference to exemplary embodiments, it is to be understood that embodiments of the present invention is not limited to the disclosed exemplary embodiments. The scope of the following claims is to be accorded the broadest interpretation so as to encompass all modifications, equivalent structures, and functions.

What is claimed is:

1. An ophthalmic imaging apparatus comprising:
   an imaging unit including an optical system configured to obtain a tomographic image of a fundus of a subject's eye by detecting an interference light beam of a measurement light beam from the fundus of the subject's eye and a reference light beam;
   a detection unit configured to detect a relative position between the imaging unit and an anterior eye portion of the subject's eye;
   a control unit configured to start, based on a result of detection by the detection unit, at least one of adjustment of an optical path length difference for driving an optical member disposed in the optical system for adjusting an optical path length difference between the measurement light beam and the reference light beam in such a manner that the tomographic image is obtained, and focus adjustment for driving an focus optical member disposed in the optical system to a focus position of the fundus of the subject's eye; and
   an adjustment unit configured to relatively adjust a positional relation between the imaging unit and the anterior eye portion of the subject's eye,
   wherein the control unit is configured to adjust, by controlling driving of the adjustment unit based on the result of detection by the detection unit, a relative positional relation between the imaging unit and the anterior eye portion of the subject's eye in such a manner that the imaging unit performs tracking for the anterior eye portion of the subject's eye, while the control unit is performing the at least one of the adjustment of the optical path length difference and the focus adjustment.

2. The ophthalmic imaging apparatus according to claim 1, wherein the control unit is configured to start the at least one of the adjustment of the optical path length difference and the focus adjustment after the relative position between the imaging unit and the anterior eye portion is adjusted.

3. The ophthalmic imaging apparatus according to claim 1, wherein the control unit is configured to perform the adjustment of the optical path length difference in such a manner that the tomographic image of the fundus is obtained, while the imaging unit is tracking the anterior eye portion.

4. An ophthalmic imaging apparatus comprising:
   an imaging unit including an optical system configured to obtain a tomographic image of a fundus of a subject's eye by using an interference light beam of a returning light beam from the fundus of the subject's eye irradiated with a measurement light beam and a reference light beam corresponding to the measurement light beam;
   a detection unit configured to detect a relative position between the imaging unit and an anterior eye portion of the subject's eye; and
   a control unit configured to adjust, based on a result of detection by the detection unit, a relative positional relation between the imaging unit and the anterior eye portion in such a manner that the imaging unit performs tracking for the anterior eye portion while at least one of optical path length difference adjustment and focus adjustment is being performed, wherein the optical path length difference adjustment is for adjusting an optical path length difference between the measurement light beam and the reference light beam, and the focus adjustment is for driving an focus optical member disposed in the optical system to a focus position of the fundus.

5. The ophthalmic imaging apparatus according to claim 4, wherein the control unit is configured to start, based on a result of detection by the detection unit, at least one of the adjustment of the optical path length difference and the focus adjustment before the tracking.

6. The ophthalmic imaging apparatus according to claim 4,
wherein the imaging unit further includes
a scanning unit provided on an optical path of the measurement light beam and configured to scan the fundus of the subject's eye with the measurement light beam;
an objective lens provided on the optical path of the measurement light beam and configured to irradiate the subject's eye with the measurement light beam from the scanning unit; and
a fundus imaging optical system configured to obtain a fundus image of the subject's eye, with the objective lens shared.

7. The ophthalmic imaging apparatus according to claim 6,
wherein the detection unit is configured to detect misalignment of the anterior eye portion based on the result of detection by the detection unit, and detect misalignment of the fundus based on the fundus image, and
wherein the control unit is configured to control the scanning unit based on the misalignment of the fundus while adjusting the relative positional relation between the imaging unit and the anterior eye portion based on the misalignment of the anterior eye portion.

8. The ophthalmic imaging apparatus according to claim 7, wherein the control unit is configured to start at least one of focus adjustment based on the fundus image, the adjustment of the optical path length difference based on a result of detecting the interference light beam, adjustment of a ratio of an intensity of the reference light beam and an intensity of the measurement light beam based on the result of detecting the interference light beam, and adjustment of a difference in polarization state between the reference light beam and the measurement light beam based on the result of detecting the interference light beam, while the control unit is adjusting the relative positional relation between the imaging unit and the anterior eye portion based on the misalignment of the anterior eye portion.

9. The ophthalmic imaging apparatus according to claim 4,
wherein the imaging unit further includes an anterior eye portion imaging optical system configured to obtain an image of the anterior eye portion;
wherein the detection unit detects the relative position on a basis of the image of the anterior eye portion.

10. The ophthalmic imaging apparatus according to claim 4,
wherein an optical member for the optical path length difference adjustment is provided on a reference light beam path for guiding the reference light beam.

11. The ophthalmic imaging apparatus according to claim 4,
wherein the optical system includes at least a measurement light beam path for guiding the measurement light beam.

12. A control method for controlling an ophthalmic imaging apparatus including an imaging unit including an optical system configured to obtain a tomographic image of a fundus of a subject's eye by detecting an interference light beam of a measurement light beam from the fundus of the subject's eye and a reference light beam, a detection unit configured to detect a relative position between the imaging unit and an anterior eye portion of the subject's eye, and an adjustment unit configured to relatively adjust a positional relation between the imaging unit and the anterior eye portion of the subject's eye, the control method comprising:
starting, based on a result of detection by the detection unit, at least one of adjustment of an optical path length difference for driving an optical member disposed in the optical system for adjusting an optical path length difference between the measurement light beam and the reference light beam in such a manner that the tomographic image is obtained, and focus adjustment for driving an focus optical member disposed in the optical system to a focus position of the fundus of the subject's eye; and
adjusting by controlling driving of the adjustment unit based on the result of detection by the detection unit, a relative positional relation between the imaging unit and the anterior eye portion of the subject's eye in such a manner that the imaging unit performs tracking for the anterior eye portion of the subject's eye, while the at least one of the adjustment of the optical path length difference and the focus adjustment is being performed.

13. The control method according to claim 12, wherein the at least one of the adjustment of the optical path length difference and the focus adjustment is started after the relative position between the imaging unit and the anterior eye portion is adjusted.

14. The control method according to claim 12, wherein the adjustment of the optical path length difference is performed in such a manner that the tomographic image of the fundus is obtained, while the imaging unit is tracking the anterior eye portion.

15. A non-transitory computer-readable storage medium storing a program that causes a computer to execute the control method for controlling the ophthalmic imaging apparatus according to claim 12.

16. A control method for controlling an ophthalmic imaging apparatus including an imaging unit including an optical system configured to obtain a tomographic image of a fundus of a subject's eye by using an interference light beam of a returning light beam from the fundus of the subject's eye irradiated with a measurement light beam and a reference light beam corresponding to the measurement light beam, and a detection unit configured to detect a relative position between the imaging unit and an anterior eye portion of the subject's eye, the control method comprising:
adjusting, based on a result of detection by the detection unit, a relative positional relation between the imaging unit and the anterior eye portion in such a manner that the imaging unit performs tracking for the anterior eye portion while at least one of optical path length difference adjustment and focus adjustment is being performed, wherein the optical path length difference adjustment is for adjusting an optical path length difference between the measurement light beam and the reference light beam, and the focus adjustment is for driving an focus optical member disposed in the optical system to a focus position of the fundus.

17. The control method according to claim 16, further comprising:
starting, based on a result of detection by the detection unit, at least one of the adjustment of the optical path length difference and the focus adjustment before the tracking.

18. A non-transitory computer-readable storage medium storing a program that causes a computer to execute the control method for controlling the ophthalmic imaging apparatus according to claim 16.

19. An ophthalmic imaging apparatus comprising:
an image forming unit configured to form a tomographic image of a subject's eye using an optical coherence tomography (OCT) optical system; and
a control unit configured to start, after completion of rough adjustment in first adjustment regarding the OCT optical system, automatic adjustment of an optical path length difference between a measurement light beam and a reference light beam, which is second adjustment regarding the OCT optical system, while the first adjustment is being performed, and to perform fine adjustment in the first adjustment and the automatic adjustment of the optical path length difference in parallel.

20. The ophthalmic imaging apparatus according to claim 19,
wherein completion of the first adjustment is completion of the fine adjustment, and
wherein completion of the second adjustment is completion of the automatic adjustment of the optical path length difference.

21. The ophthalmic imaging apparatus according to claim 19, further comprising an OCT focus optical member disposed in the OCT optical system,
wherein the first adjustment is automatic focus adjustment using the OCT focus optical member.

22. The ophthalmic imaging apparatus according to claim 21,
wherein a focus range in which the OCT focus optical member is moved is smaller in the fine adjustment than in the rough adjustment.

23. The ophthalmic imaging apparatus according to claim 22, further comprising a determination unit configured to determine the focus range in the fine adjustment based on a result of the rough adjustment.

24. The ophthalmic imaging apparatus according to claim 21,
wherein a focus distance that is a moving amount of the OCT focus optical member is shorter in the fine adjustment than in the rough adjustment.

25. The ophthalmic imaging apparatus according to claim 21, further comprising a Scanning Laser Ophthalmoscopes (SLO) focus optical member disposed in an SLO optical system,
wherein the control unit is configured to perform automatic focus adjustment using the SLO focus optical member and the first adjustment based on SLO information obtained by the SLO optical system.

26. The ophthalmic imaging apparatus according to claim 25,
wherein the control unit is configured to perform the first adjustment in conjunction with the automatic focus adjustment using the SLO focus optical member.

27. The ophthalmic imaging apparatus according to claim 19, further comprising:
an imaging unit including at least a measurement optical path for guiding the measurement light and including the OCT optical system configured to obtain a tomographic image of a fundus of the subject's eye by detecting an interference light beam of the measurement light beam from the fundus and the reference light beam; and
a detection unit configured to detect a relative position between the imaging unit and an anterior eye portion of the subject's eye,
wherein the control unit is configured to adjust, based on a result of detection by the detection unit, a relative positional relation between the imaging unit and the anterior eye portion in such a manner that the imaging unit performs tracking for the anterior eye portion while at least one of the first adjustment and the second adjustment is being performed.

28. The ophthalmic imaging apparatus according to claim 27,
wherein the imaging unit further includes
a scanning unit disposed in the measurement optical path and configured to scan the fundus of the subject's eye with the measurement light beam,
an objective lens disposed in the measurement optical path and configured to irradiate the subject's eye with the measurement light beam from the scanning unit, and
a fundus imaging optical system for capturing a fundus image of the subject's eye, using the objective lens in common.

29. The ophthalmic imaging apparatus according to claim 28,
wherein the detection unit is configured to detect misalignment of the anterior eye based on a result of detection by the detection unit and to detect misalignment of the fundus based on the fundus image, and
wherein the control unit is configured to control the scanning unit based on the misalignment of the fundus while adjusting the relative positional relation between the imaging unit and the anterior eye based on the misalignment of the anterior eye.

30. The ophthalmic imaging apparatus according to claim 29,
wherein the imaging unit further includes an anterior eye imaging optical system configured to capture an image of the anterior eye, and
wherein the detection unit is configured to detect the relative position based on the image of the anterior eye.

31. A control method for controlling an ophthalmic imaging apparatus, the control method comprising:
forming a tomograhic image of a subject's eye using an optical coherence tomography (OCT) optical system;
starting, after completion of rough adjustment in first adjustment regarding the OCT optical system, automatic adjustment of an optical path length difference between a measurement light beam and a reference light beam, which is second adjustment regarding the OCT optical system, while the first adjustment is being performed; and
performing fine adjustment in the first adjustment and the automatic adjustment of the optical path length difference in parallel.

32. A non-transitory computer-readable storage medium storing a program that causes a computer to execute the control method for controlling the ophthalmic imaging apparatus according to claim 31.

* * * * *